United States Patent [19]

Fehr et al.

[11] Patent Number: 5,185,318
[45] Date of Patent: Feb. 9, 1993

[54] AROMATIC COMPOUNDS, A PROCESS FOR PREPARATION THEREOF AND USE OF SAME AS PERFUMING INGREDIENTS

[75] Inventors: Charles Fehr, Versoix; José Galindo, Les Avanchets, both of Switzerland

[73] Assignee: Firmenich S.A., Geneva, Switzerland

[21] Appl. No.: 817,223

[22] Filed: Jan. 6, 1992

Related U.S. Application Data

[62] Division of Ser. No. 544,285, Jun. 26, 1990.

Foreign Application Priority Data

Jun. 30, 1989 [CH] Switzerland ............... 2454/89

[51] Int. Cl.$^5$ ................................. A61K 7/46
[52] U.S. Cl. ..................... 512/16; 252/174.11; 252/8.6; 424/76.4; 512/17
[58] Field of Search ............................. 512/21

[56] References Cited

U.S. PATENT DOCUMENTS

| | | | |
|---|---|---|---|
| 3,045,047 | 7/1962 | Davidson et al. ............ | 568/377 |
| 3,393,994 | 7/1968 | Achuff ........................... | 71/123 |
| 3,499,751 | 3/1970 | Wood et al. .................... | 71/123 |
| 4,001,330 | 1/1977 | Curran ........................... | 568/377 |
| 4,284,819 | 8/1981 | Sprecker et al. ............... | 512/20 |
| 4,885,274 | 12/1989 | Yamada et al. ................. | 512/16 |

FOREIGN PATENT DOCUMENTS

| | | | |
|---|---|---|---|
| 1543065 | 12/1970 | Fed. Rep. of Germany ...... | 512/20 |
| 2408689 | 7/1974 | Fed. Rep. of Germany ...... | 512/20 |
| 1148499 | 10/1957 | France . | |
| 1392804 | 3/1964 | France ........................... | 512/20 |
| 760667 | 11/1956 | United Kingdom ............. | 512/20 |
| 787541 | 12/1957 | United Kingdom ............. | 512/20 |
| 788132 | 12/1957 | United Kingdom ............. | 512/20 |

OTHER PUBLICATIONS

M.G.J. Beets, *Structure–Activity Relationships in Human Chemoreception*, Applied Science Publishers, §9.2, pp. 214–228 (1978).
C. Fehr et al., "New Aromatic Musk Odorants, Design and Synthesis," Helvetica Chemica Acta, vol. 72, No. 173, 1989.

*Primary Examiner*—James H. Reamer
*Attorney, Agent, or Firm*—Pennie & Edmonds

[57] ABSTRACT

Compound of formula

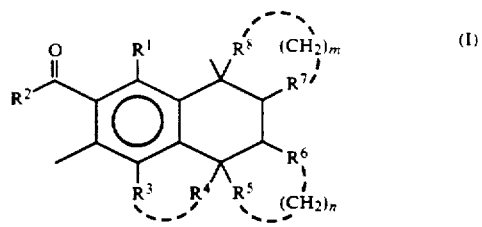

wherein a) indexes m and n are identical and stand each for an integer number equal to zero, symbols $R^1$ and $R^2$ are identical and represent each a hydrogen atom, or are different and represent each a hydrogen atom or a methyl radical, symbols $R^5$ and $R^8$ stand each for a methyl radical, symbols $R^6$ and $R^7$ can be identical or different and designate each a hydrogen atom or a methyl radical and, either symbol $R^4$ represents a methyl radical and symbol $R^3$ stands for a hydrogen atom or a methyl radical, or symbols $R^3$ and $R^4$ represent each a methylene radical belonging to a ring such as indicated by the dotted line, with the proviso that the following combinations are excluded:

1. $R^1 = R^2 = R^3 = R^6 = R^7 = H$, or
2. $R^1 = R^2 = R^3 = H$ and $R^6$ or $R^7 = CH_3$, or
3. $R^2 = CH_3$ and $R^3 = R^6 = R^7 = H$, or
4. $R^2 = CH_3$ and $R^3 = H$ and $R^6$ or $R^7 = CH_3$, or
5. $R^1 = R^3 = CH_3$, or
6. $R^3 = R^4 = CH_2$ and $R^2$ or $R^7 = CH_3$;

or wherein b) indexes m and n are different and define each an integer number equal to 0 or 1, symbol $R^2$ stands for a hydrogen atom or a methyl radical, symbols $R^1$ and $R^3$ designates each a hydrogen atom, symbol $R^4$ represents a methyl radical and, either symbols $R^5$ and $R^6$ are identical (n=1) and represent each a methylene radical belonging to a ring such as indicated by the dotted line, $R^7$ representing a hydrogen atom and $R^8$ a methyl radical, or symbol $R^5$ stands for a methyl radical and symbol $R^6$ for a hydrogen atom, $R^7$ and $R^8$ being then identical (m=1) and designating each a methylene radical belonging to a ring such as indicated by the dotted line;

or any mixture of two or more structural isomers of formula (I).

Compounds (I) develop odor notes or the musky type and can therefore be used as active ingredients in perfruming compositions and perfumed articles of varied nature.

A process for the preparation of compound (I) is described.

8 Claims, No Drawings

AROMATIC COMPOUNDS, A PROCESS FOR PREPARATION THEREOF AND USE OF SAME AS PERFUMING INGREDIENTS

This is a division of application Ser. No. 07/544,285, filed Jun. 26, 1990.

BRIEF SUMMARY OF THE INVENTION

The present invention relates to the field of perfumery and, more particularly, to a special group of novel aromatic compounds which possess musky odor notes and are represented by the formula

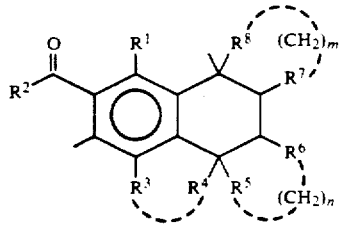

wherein a) indexes m and n are identical and stand each for an integer number equal to zero, symbols $R^1$ and $R^2$ are identical and represent each a hydrogen atom, or are different and represent each a hydrogen atom or a methyl radical, symbols $R^5$ and $R^8$ stand each for a methyl radical, symbols $R^6$ and $R^7$ can be identical or different and designate each a hydrogen atom or a methyl radical and, either symbol $R^4$ represents a methyl radical and symbol $R^3$ stands for a hydrogen atom or a methyl radical, or symbols $R^3$ and $R^4$ represent each a methylene radical belonging to a ring such as indicated by the dotted line, with the proviso that the following combinations are excluded:

1. $R^1 = R^2 = R^3 = R^6 = R^7 = H$, or
2. $R^1 = R^2 = R^3 = H$ and $R^6$ or $R^7 = CH_3$, or
3. $R^2 = CH_3$ and $R^3 = R^6 = R^7 = H$, or
4. $R^2 = CH_3$ and $R^3 = H$ and $R^6$ or $R^7 = CH_3$, or
5. $R^1 = R^3 = CH_3$, or
6. $R^3 = R^4 = CH_2$ and $R^2$ or $R^7 = CH_3$;

or wherein b) indexes m and n are different and define each an integer number equal to 0 or 1, symbol $R^2$ stands for a hydrogen atom or a methyl radical, symbols $R^1$ and $R^3$ designate each a hydrogen atom, symbol $R^4$ represents a methyl radical and, either symbols $R^5$ and $R^6$ are identical (n=1) and represent each a methylene radical belonging to a ring such as indicated by the dotted line, $R^7$ representing a hydrogen atom and $R^8$ a methyl radical, or symbol $R^5$ stands for a methyl radical and symbol $R^6$ for a hydrogen atom, $R^7$ and $R^8$ being then identical (m=1) and designating each a methylene radical belonging to a ring such as indicated by the dotted line; or any mixture of two or more structural isomers of formula (I).

The invention further relates to a method to improve, enhance or modify the odor properties of a perfuming composition or a perfumed article, which process comprises adding to said composition or article an effective amount of a compound of formula (I) defined above.

Another object of the invention is to provide a perfuming composition or a perfumed article containing a compound of formula (I) as a perfuming ingredient.

The invention also relates to a process for the preparation of a compound of formula (I), which process comprises:

A. a) the reaction, under the action of light, of a compound of formula

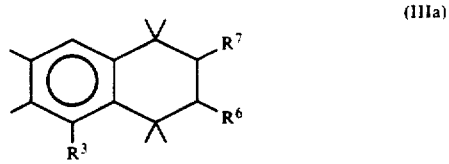

wherein symbols $R^3$, $R^6$ and $R^7$ can be identical or different and represent each a hydrogen atom or a methyl radical, with a halogenation agent to obtain a mixture of halides of formula

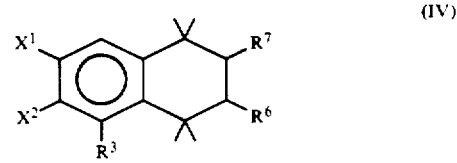

wherein symbols $R^6$ and $R^7$ are defined as above, symbol $R^3$ stands for a hydrogen atom, a halogen atom ($X^1 = X^2 = CH_3$) or a methyl radical, and symbols $X^1$ and $X^2$ are identical and designate each a methyl radical ($R^3 =$ halogen) or are different ($R^3 = H, CH_3$) and represent each a halogen atom or a methyl radical;

b) the hydrolysis of said mixture of halides to obtain a mixture of corresponding alcohols, and the subsequent oxidation of the latter mixture to provide a mixture of aldehydes of formula

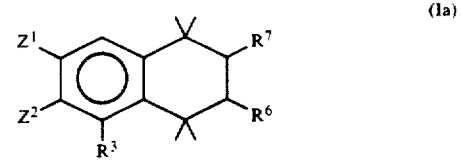

wherein symbols $R^6$ and $R^7$ are defined as above, symbol $R^3$ represents a hydrogen atom or a methyl radical, or a CHO group when $Z^1 = Z^2 = CH_3$, and symbols $Z^1$ and $Z^2$ are identical and designate each a methyl radical when $R^3 = CHO$, or are different and represent each a CHO group or a methyl radical when $R^3 = H$ or $CH_3$; and c) the separation of said aldehydes from the reaction mixture, followed by the treatment of said aldehydes successively with MeLi or MeMgX (Me=CH_3, X=halogen), $H_2O$ and an oxidation agent, to obtain ketones of formula

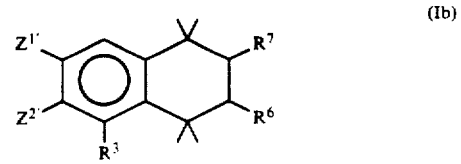

wherein symbols $R^6$ and $R^7$ are defined as above, symbol $R^3$ represents a hydrogen atom, a methyl radical or a CH₃CO group (Z¹=Z²=CH₃), and symbols Z¹ and Z² are identical and designate each a methyl radical (R³=CH₃CO) or are different and represent each a CH₃CO group or a methyl radical (R³=H, CH₃); or B. a) the reaction of a compound of formula

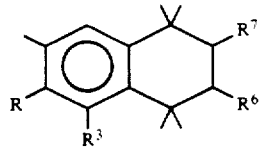
(IIIb)

wherein symbols R and R³ are different and represent each a hydrogen atom or a methyl radical and symbols R⁶ and R⁷ are defined as above, with an oxidation or formylation agent to obtain an aldehyde of formula

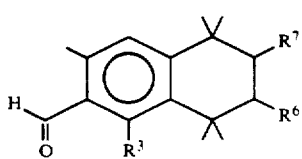
(Ic)

wherein symbol R³ represents a hydrogen atom or a methyl radical; and b) the treatment of aldehyde (Ic) with MeI or a Grignard reagent followed by a hydrolysis and an oxidation to obtain a ketone of formula

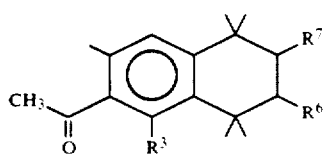
(Id)

wherein symbols R³, R⁶ and R⁷ designate each a hydrogen atom or a methyl radical; or C. the reaction of a compound of formula

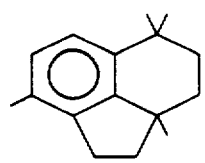
(IIIc)

or of a mixture of compounds of formula

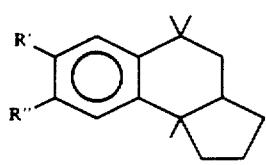
(IIId)

wherein symbols R' and R" are different and represent each a hydrogen atom or a methyl radical, with Cl₂CHOCH₃, under the Friedel-Crafts acylation reaction conditions, to obtain respectively an aldehyde of formula

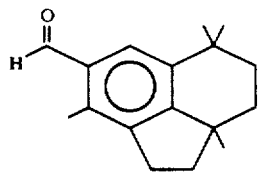
(Ie)

or a mixture of aldehydes of formula

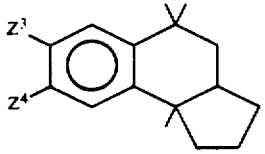
(If)

wherein symbols Z³ and Z⁴ are different and represent each a CHO group or a methyl radical; or with acetyl chloride, in the presence of a Lewis acid, to obtain respectively a ketone of formula

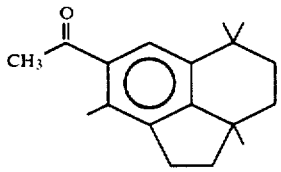
(Ig)

or a mixture of ketones of formula

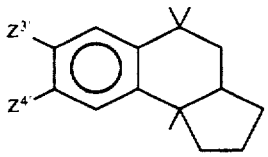
(Ih)

wherein symbols Z³' and Z⁴' are different and designate each a CH₃CO group or a methyl radical.

Finally, the invention also provides novel compounds of formula

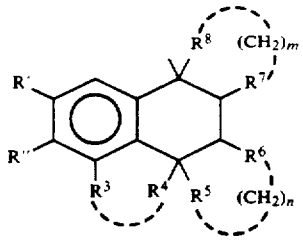
(III)

wherein a) indexes m and n define identical integer numbers equal to zero, symbols R⁵ and R⁸ represent each a methyl radical, symbols R⁶ and R⁷ can be identical or different and represent each a hydrogen atom or a methyl radical, and either symbol R⁴ represents a methyl radical, symbols R' and R" are identical and stand for a methyl radical and symbol R³ represents a hydrogen atom or a methyl radical, or symbol R⁴ designates a methyl radical, symbol R" a hydrogen atom and symbols R' and R³ each a methyl radical, or R³ and R⁴ are identical and designate each a methylene radical belonging to a ring such as indicated by the dotted line and R' and R" designate respectively a hydrogen atom and a methyl radical, with the proviso that the following combination is excluded:

1. $R^3 = R^4 = CH_2$ and $R^6$ or $R^7 = CH_3$;

or wherein b) indexes m and n are different and define each an integer number equal to 0 or 1, symbols R' and R" represent respectively a hydrogen atom and a methyl radical, symbol $R^3$ stands for a hydrogen atom, symbol $R^4$ for a methyl radical and, either symbols $R^5$ and $R^6$ are identical (n=1) and stand each for a methylene group belonging to a ring such as represented by the dotted line, symbol $R^7$ designating a hydrogen atom and symbol $R^8$ a methyl radical, or $R^5$ designates a methyl radical and $R^6$ a hydrogen atom, $R^7$ and $R^8$ being then identical (m=1) and standing each for a methylene radical belonging to a cycle such as represented by the dotted line, or any mixture of two or more structural isomers of formula (III).

BACKGROUND OF THE INVENTION

The search for novel compounds with a musky odor has increased steadily in the last few years, as a result of the privileged position that this type of fragrant compounds occupies in modern perfumery. Several hundreds of these compounds are known today, forming a rich source of structural information which has lead certain authors to establish qualitative rules intended for predicting which types of chemical structures are more likely to provide good quality musky compounds, judging from the intensity, the tenacity or the elegance and individuality of their odor note. Although these rules can prove helpful for finding a few more or less interesting compounds, they do not constitute an ersatz for the researcher's inventive mind, which reveals itself all the more pertinent when it follows, by intuition, a discovery path that would have been discouraged by said principles built on the basis of the known prior art. As it will become apparent shortly, the present invention is just an example of this.

It is generally accepted that, in musky aromatic compounds whose benzene ring possesses an acyl group substituent, sterical hindrance of this functional group can lead to loss of odor [see, for example, M. J. Beets, Structure-Activity Relationships in Human Chemoreception, 207, ASP Ltd. London (1978)]. Thus, any attempt to further substitute the benzene ring in the following basic structural skeleton for the aromatic compounds of interest

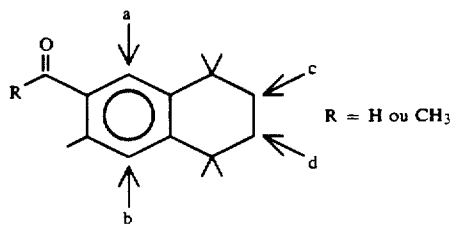

R = H ou $CH_3$ would have been discouraged from the start. There are several musky compounds already known which obey this basic structure, the best known representative thereof being Tonalid ® (origin: Polak's Frutal Works Inc.), which has the following structure

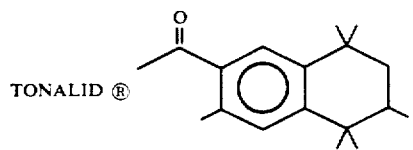

TONALID ® and is well appreciated in the perfume industry.

Unlike what could have been expected from prior art predictions, we have now discovered that further methyl and methylene groups can be incorporated in position a or b (see skeleton above) of the benzene ring without observing any prejudicial effect on the odor properties of the resulting compounds, in spite of the ensuing perturbation of the functional group's environment. On the contrary, several excellent novel musky compounds have thus been discovered.

THE INVENTION

The present invention provides novel aromatic compounds of formula

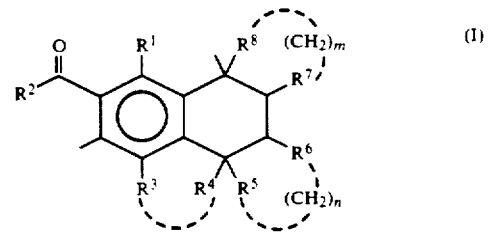

wherein a) indexes m and n are identical and stand each for an integer number equal to zero, symbols $R^1$ and $R^2$ are identical and represent each a hydrogen atom, or are different and represent each a hydrogen atom or a methyl radical, symbols $R^5$ and $R^8$ stand each for a methyl radical, symbols $R^6$ and $R^7$ can be identical or different and designate each a hydrogen atom or a methyl radical and, either symbol $R^4$ represents a methyl radical and symbol $R^3$ stands for a hydrogen atom or a methyl radical, or symbols $R^3$ and $R^4$ represent each a methylene radical belonging to a ring such as indicated by the dotted line, with the proviso that the following combinations are excluded:

1. $R^1 = R^2 = R^3 = R^6 = R^7 = H$, or
2. $R^1 = R^2 = R^3 = H$ and $R^6$ or $R^7 = CH_3$, or
3. $R^2 = CH_3$ and $R^3 = R^6 = R^7 = H$, or
4. $R^2 = CH_3$ and $R^3 = H$ and $R^6$ or $R^7 = CH_3$, or
5. $R^1 = R^3 = CH_3$, or
6. $R^3 = R^4 = CH_2$ and $R^2$ or $R^7 = CH_3$;

or wherein b) indexes m and n are different and define each an integer number equal to 0 or 1, symbol $R^2$ stands for a hydrogen atom or a methyl radical, symbols $R^1$ and $R^3$ designate each a hydrogen atom, symbol $R^4$ represents a methyl radical and, either symbols $R^5$ and $R^6$ are identical (n=1) and represent each a methylene radical belonging to a ring such as indicated by the dotted line, $R^7$ representing a hydrogen atom and $R^8$ a methyl radical, or symbol $R^5$ stands for a methyl radical and symbol $R^6$ for a hydrogen atom, $R^7$ and $R^8$ being then identical (m=1) and designating each a methylene radical belonging to a ring such as indicated by the dotted line;

or any mixture of two or more structural isomers of formula (I).

We have discovered that compounds (I) possess very interesting odor properties and that they can be used for the preparation of perfuming compositions and perfumed articles. As a result of the richness and quality of their musky odor notes, they are particularly suited to the preparation of perfuming bases and concentrates intended for masculine type perfumes and Colognes, as well as shaving lotions. In addition, they are equally appreciated for perfuming soaps, shower and bath gels, shampoos and hair care products, cosmetic preparations and body deodorants. Furthermore, their use in detergents and fabric softeners is especially advantageous, since the excellent substantivity of their musky odor note ensures an efficient perfuming of the textiles treated with these products, which is also longlasting.

As it has already been pointed out, in view of the prior art, the high quality of the odor notes exhibited by these compounds was totally unexpected. Furthermore, we were also surprised to find that the incorporation of methyl and methylene groups in positions c and/or d of the benzene ring in the same basic structural skeleton above-mentioned, eventually simultaneous with the substitution in positions a and b, could lead to novel aromatic musky compounds of formula (I) possessing truly remarkable odor properties.

We observed, in fact, that the incorporation of additional methyl and methylene groups in the basic structural skeleton of this type of fragrant compounds does not seem to cause substantial modification in the overall shape of the molecule, unlike what could have been predicted, and leads to more or less spherical structures, highly dense and of improved lipophilicity, which turn out to be remarkably powerful musky compounds, whose fragrance is stronger than that of the prior art compounds. This, in turn, means that multiple alkyl or alkenyl substitution of the basic skeleton, namely in the lipophilic part of the molecule (positions c and d), can cause strong and quite advantageous changes in the organoleptic properties of these fragrant compounds, an observation that had not been sufficiently recognized up to now.

A particularly interesting example is that of the compounds of the invention having the formula

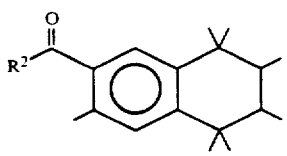

(II)

wherein $R^2$ designates a hydrogen atom or a methyl group. The two compounds obeying this formula possess quite distinct odor notes, which are also stronger than that of Tonalid ®.

The aldehydic compound of formula (II) is characterized by a musky-amber-animal note reminiscent of natural musk. It further possesses an earthy note resembling that of Cashmeran (6,7-dihydro-1,1,2,3,3-pentamethyl-4(5H)-indanone; origin: International Flavors & Fragrances Inc.) but which is much more powerful than the latter. In addition, the fragrance of the compound of the invention also shows an aspect characteristic of the nitro-aromatic musky compounds which renders said compound of the invention all the more interesting, in view of the fact that nitro-aromatic musks are gradually disappearing from the perfumer's palette. It is not only a powerful odor note, far superior to the notes of the musky compounds already available on the market, but also a tenacious and substantive note, as can be assessed from the comparative examples described further on.

As for the ketone compound (II), it develops a quite different fragrance, showing practically none of the earthy-rooty character found in its aldehydic homologue cited above and possessing instead a finer, more classical and slightly animal musky note, devoid of the amber character. Although its odor note is less powerful than that of the aldehyde, it is still comparable, in strength, to those of the best musky compounds available on the market, while having a different character.

These two compounds of formula (II), or 5,6,7,8-tetrahydro-3,5,5,6,7,8,8-heptamethyl-2-naphthalenecarbaldehyde and (5,6,7,8-tetrahydro-3,5,5,6,7,8,8-heptamethyl-2-naphthyl)-1-ethanone, can assume two isomeric forms, i.e., cis and trans. In the case of the aldehyde, these two forms have been separated by gas chromatography and evaluated individually. As for the ketone homologue, only the trans isomer could be separated from the mixture containing both isomers. These isomer mixtures directly obtained from the synthesis of compounds (I) are also quite excellent odoriferous compounds and can be used directly for the preparation of perfuming compositions and perfumed products according to the invention.

Other preferred compounds of the invention include:
a) 5,6,7,8-tetrahydro-1,3,5,5,8,8-hexamethyl-2-naphthalenecarbaldehyde
b) 5,6,7,8-tetrahydro-3,4,5,5,8,8-hexamethyl-2-naphthalenecarbaldehyde
c) 5,6,7,8-tetrahydro-1,3,5,5,6,8,8-heptamethyl-2-naphthalenecarbaldehyde
d) 5,6,7,8-tetrahydro-3,4,5,5,7,8,8-heptamethyl-2-naphthalenecarbaldehyde
e) 5,6,7,8-tetrahydro-1,3,5,5,7,8,8-heptamethyl-2-naphthalenecarbaldehyde
f) 5,6,7,8-tetrahydro-3,4,5,5,6,8,8-heptamethyl-2-naphthalenecarbaldehyde
g) 1,2,6,7,8,8a-hexahydro-3,6,6,8a-tetramethyl-4-acenaphthylenecarbaldehyde
h) (1,2,6,7,8,8a-hexahydro-3,6,6,8a-tetramethyl-4-acenaphthylenyl)ethanone All these compounds possess musky notes of varied strength and substantivity, with character differences which can be more or less marked. Their specific odor properties are described in detail in the context of the respective preparation examples appearing further on.

In addition, the synthesis of compounds (I) can lead to mixtures of compounds a) and b), or c) and d), or e) and f). Such mixtures were found to be perfectly adequate for use in perfumery applications according to the invention.

One can further cite, as preferred compounds according to the invention, the mixtures of the following compounds i) and j) or k) and l):
i) 2,3,3a,4,5,9b-hexahydro-5,5,8,9b-tetramethyl-1H-benz[e]indene-7-carbaldehyde
j) 2,3,3a,4,5,9b-hexahydro-5,5,7,9b-tetramethyl-1H-benz[e]indene-8-carbaldehyde
k) 1-(2,3,3a,4,5,9b-hexahydro-5,5,8,9b-tetramethyl-1H-benz[e]inden-7-yl)-1-ethanone
l) 1-(2,3,3a,4,5,9b-hexahydro-5,5,7,9b-tetramethyl-1H-benz[e]inden-8-yl)-1-ethanone.

The odor properties of these mixtures are also described in detail in the corresponding preparation examples.

The concentrations in which the compounds of formula (I) can be used to achieve the desired perfuming effects can vary in a wide range of values. The man in the art knows by experience that such concentration values are a function of the specific effect one wants to achieve, as well as of the nature of the article to be perfumed. It is also well known that such values depend on the nature of other co-ingredients in a given composition, when a compound according to the invention is used in a perfume base or concentrate in admixture with other perfuming ingredients, solvents or the usual adjuvants.

For the sake of example, concentrations of the order of 5, 10 or even 20% by weight, relative to the weight of composition, can be cited, when the compounds (I) are incorporated into a perfuming base or concentrate. These values can be much smaller when compounds (I) are used as perfuming ingredients in articles such as soaps, cosmetic preparations or detergents.

According to the invention, a compound of formula (I) can be used in these perfumery applications either alone, by directly adding said compound to the article to be perfumed, or, more commonly, in admixture with other perfuming ingredients currently used in the perfume industry. A specific citation of such co-ingredients is not warranted here. One can find many examples in the prior art and the man in the art is able to choose such ingredients as are more appropriate to produce the desired perfuming effect. In this context one can cite as a prior art of reference the book by S. Arctander, Perfume and Flavor Chemicals, Montclair, N.J., USA (1969).

Furthermore, as already mentioned, perfuming compositions and perfumed articles according to the invention can be prepared by using as active ingredient one of the mixtures of compounds (I) already cited, or yet any other mixture of compounds of formula (I).

Amongst the articles advantageously perfumed with compounds (I), one can cite perfumes and colognes, namely masculin type ones, as well as shaving lotions, soaps, shower and bath gels, shampoos, cosmetic preparations or detergents and fabric softerners.

The present invention further provides an original process for the preparation of compounds of formula (I). In spite of the prior art knowledge related to the synthesis of musky aromatic compounds, that of the compounds according to the instant invention turned out to present specific problems in so far as it involved the preparation of sterically hindered molecules.

The process according to the invention for the preparation of compounds of formula (I) comprises:

A. a) the reaction, under the action of light, of a compound of formula

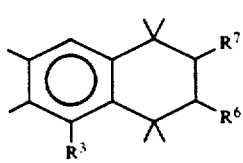

(IIIa)

wherein symbols $R^3$, $R^6$ and $R^7$ can be identical or different and represent each a hydrogen atom or a methyl radical, with a halogenation agent to obtain a mixture of halides of formula

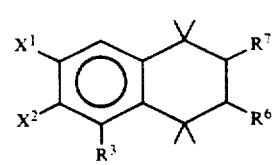

(IV)

wherein symbols $R^6$ and $R^7$ are defined as above, symbol $R^3$ stands for a hydrogen atom, a halogen atom ($X^1=X^2=CH_3$) or a methyl radical, and symbols $X^1$ and $X^2$ are identical and designate each a methyl radical ($R^3$=halogen) or are different ($R^3$=H, $CH_3$) and represent each a halogen atom or a methyl radical;

b) the hydrolysis of said mixture of halides to obtain a mixture of corresponding alcohols, and the subsequent oxidation of the latter mixture to provide a mixture of aldehydes of formula

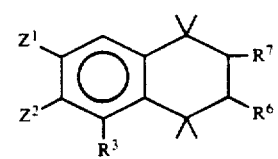

(Ia)

wherein symbols $R^6$ and $R^7$ are defined as above, symbol $R^3$ represents a hydrogen atom or a methyl radical, or a CHO group when $Z^1=Z^2=CH_3$ and symbols $Z^1$ and $Z^2$ are identical and designate each a methyl radical when $R^3$=CHO, or are different and represent each a CHO group or a methyl radical when $R^3$=H or $CH_3$; and c) the separation of said aldehydes from the reaction mixture, followed by the treatment of said aldehydes successively with MeLi or MeMgX (Me=$CH_3$, X=halogen), $H_2O$ and an oxidation agent, to obtain ketones of formula

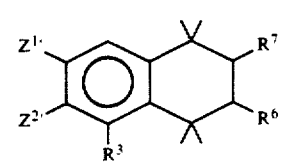

(Ib)

wherein symbols $R^6$ and $R^7$ are defined as above, symbol $R^3$ represents a hydrogen atom, a methyl radical or a $CH_3CO$ group ($Z^{1'}=Z^{2'}=CH_3$), and symbols $Z^{1'}$ and $Z^{2'}$ are identical and designate each a methyl radical ($R^3=CH_3CO$) or are different and represent each a $CH_3CO$ group or a methyl radical ($R^3$=H, $CH_3$); or B. a) the reaction of a compound of formula

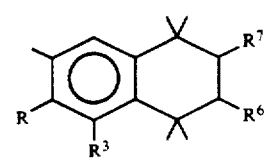

(IIIb)

wherein symbols R and $R^3$ are different and represent each a hydrogen atom or a methyl radical and symbols $R^6$ and $R^7$ are defined as above, with an oxidation or formylation agent to obtain an aldehyde of formula

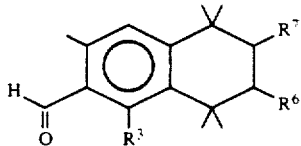

wherein symbol $R^3$ represents a hydrogen atom or a methyl radical; and b) the treatment of aldehyde (Ic) with MeI or a Grignard reagent followed by a hydrolysis and an oxidation to obtain a ketone of formula

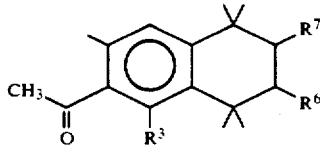

wherein symbols $R^3$, $R^6$ and $R^7$ designate each a hydrogen atom or a methyl radical; or C. the reaction of a compound of formula

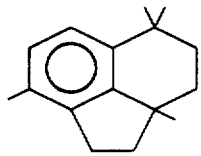

or of a mixture of compounds of formula

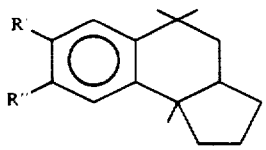

wherein symbols R' and R" are different and represent each a hydrogen atom or a methyl radical, with $Cl_2CHOCH_3$, under the Friedel-Crafts acylation reaction conditions, to obtain respectively an aldehyde of formula

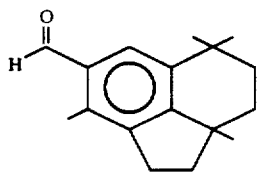

or a mixture of aldehydes of formula

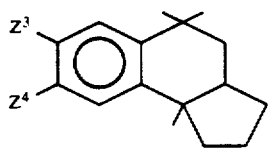

wherein symbols $Z^3$ and $Z^4$ are different and represent each a CHO group or a methyl radical; or with acetyl chloride, in the presence of a Lewis acid, to obtain respectively a ketone of formula

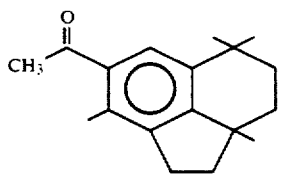

or a mixture of ketones of formula

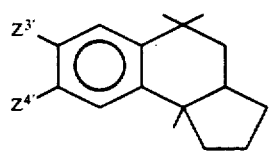

wherein symbols $Z^{3'}$ and $Z^{4'}$ are different and designate each a $CH_3CO$ group or a methyl radical.

The starting products in this process are novel hydrocarbons of formula

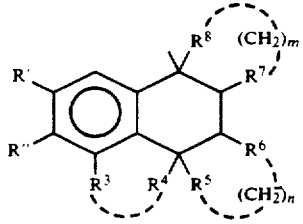

wherein a) indexes m and n define identical integer numbers equal to zero, symbols $R^5$ and $R^8$ represent each a methyl radical, symbols $R^6$ and $R^7$ can be identical or different and represent each a hydrogen atom or a methyl radical, and either symbol $R^4$ represents a methyl radical, symbols R' and R" are identical and stand each for a methyl radical and symbol $R^3$ represents a hydrogen atom or a methyl radical, or symbol $R^4$ designates a methyl radical, symbol R" a hydrogen atom and symbols R' and $R^3$ each a methyl radical, or $R^3$ and $R^4$ are identical and designate each a methylene radical belonging to a ring such as indicated by the dotted line and R' and R" designate respectively a hydrogen atom and a methyl radical, with the proviso that the following combination is excluded:

1. $R^3 = R^4 = CH_2$ and $R^6$ or $R^7 = CH_3$;

or wherein b) indexes m and n are different and define each an integer number equal to 0 or 1, symbols R' and R" represent respectively a hydrogen atom and a methyl radical, symbol $R^3$ stands for a hydrogen atom, symbol $R^4$ for a methyl radical and, either symbols $R^5$ and $R^6$ are identical (n=1) and stand each for a methylene group belonging to a ring such as represented by the dotted line, symbol $R^7$ designating a hydrogen atom and symbol $R^8$ a methyl radical, or $R^5$ designates a methyl radical and $R^6$ a hydrogen atom, $R^7$ and $R^8$ being then identical (m=1) and standing each for a methylene radical belonging to a cycle such as represented by the dotted line, or any mixture of two or more structural isomers of formula (III).

Hydrocarbons (II) can be converted into the desired compounds of formula (I) following methods which involve classical reactions of the above-mentioned type. Several combinations of such reactions can be used to prepare the compounds of formula (I) but one or another of said combinations will be preferred, depending on the structure of the desired final product.

Thus, when compounds of formula (Ia) or (Ib) are to be prepared, one will typically use a starting hydrocarbon of formula (III), which will be preferentially treated as represented in the following reaction scheme:

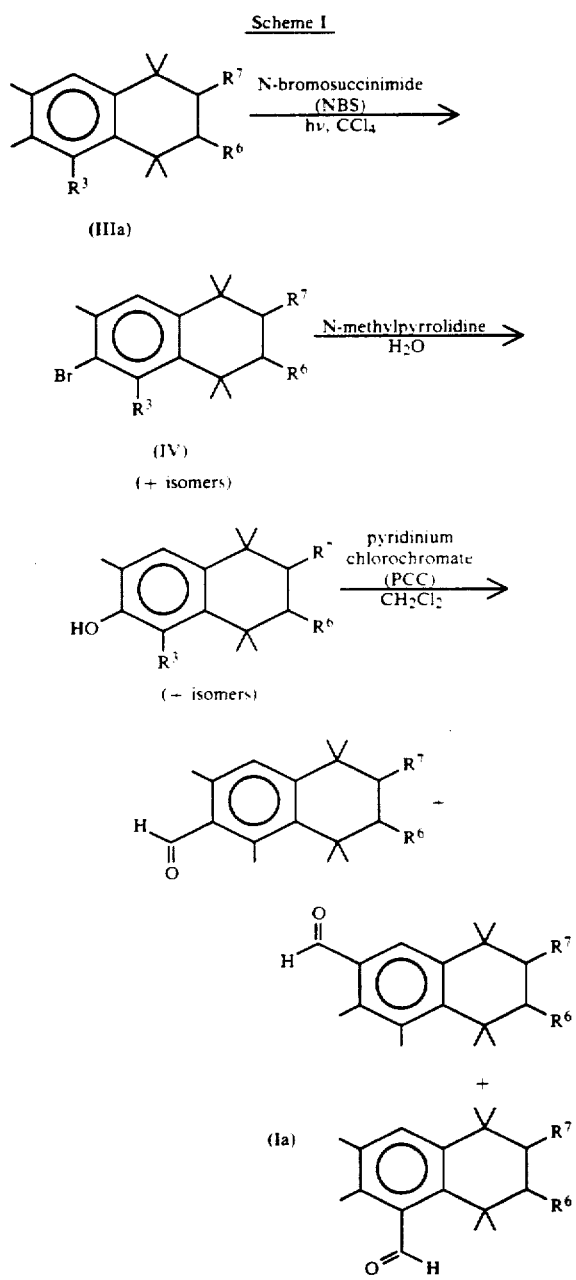

$R^3$, $R^6$ and $R^7$, in each step, are defined as above

Aldehydes of structure (Ia) can be separated from the obtained mixture by the usual separation techniques such as, for example, gas chromatography. These aldehydes can also be converted into the corresponding ketones of formula (Ib) through alkylation in the presence of $CH_3Li$ in ether, followed by hydrolysis and oxidation of the resulting alcohol, for example by means of pyridinium chlorochromate in dichloromethane.

The starting products of formula (IIIa) can be prepared from benzene derivatives following a multistep process represented in Scheme II and which resorts to the use of a combination of reactions described by T. F. Wood and P. O. Roblin [see, for example, T. F. Wood et al., J. Org. Chem. 28, 2248 (1963)]:

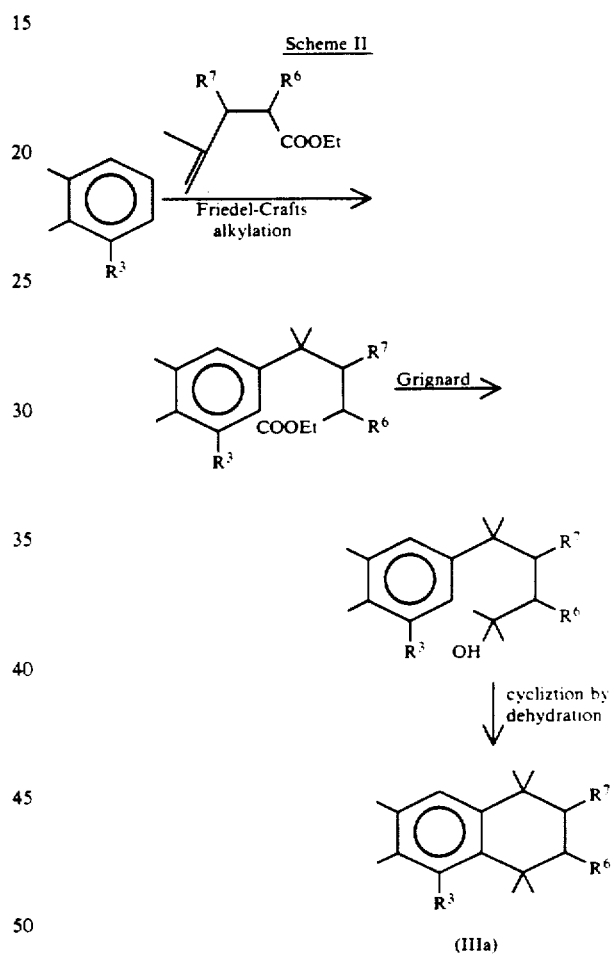

$R^3$, $R^6$ and $R^7$ represent H or $CH_3$
Et = $CH_2CH_3$

Typically, the Lewis acid used in the alkylation reaction will be aluminium trichloride and, the Grignard reagent used in the following step, $CH_3MgI$. The cyclisation reaction is an acid catalyzed reaction, typically by $H_2SO_4$. The ethyl ethers used in the alkylation step can be obtained by conventional methods described in detail in the preparation examples presented further on.

We observed that compounds of formula (IIIa) wherein $R^6 = R^7 = H$ could be prepared more advantageously by an original process, illustrated in the following reaction scheme:

Scheme III

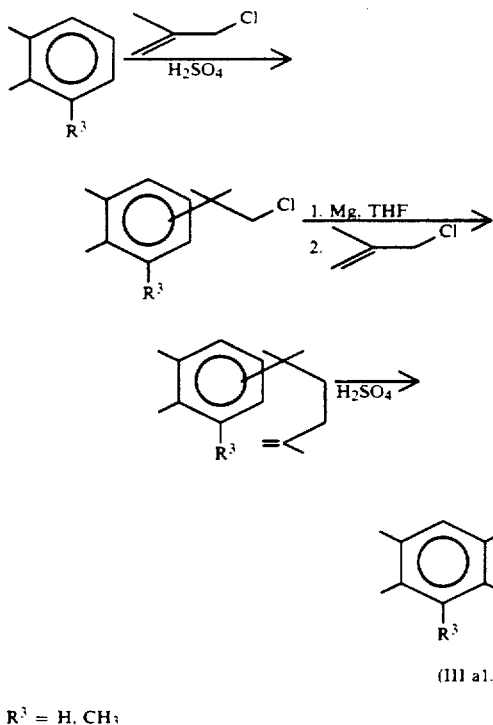

(III a1.)

$R^3 = H, CH_3$

It consists of a reaction sequence comprising the coupling of two halides, followed by an intramolecular alkylation, in acidic medium, which has the advantage of avoiding the use of a Lewis acid. In addition, it is a cheaper process, which also produces less residues.

In the case of the synthesis of compounds (II) according to the invention, and more particularly that of the mixtures containing the two isomeric forms of these compounds already cited, we discovered that one could use preferentially the process represented in Scheme IV leading directly to mixtures of the appropriate precursors (III b1.) and (III b2.):

Scheme IV

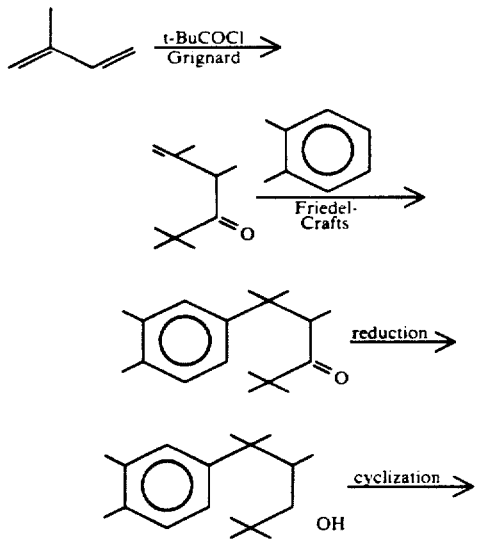

-continued
Scheme IV

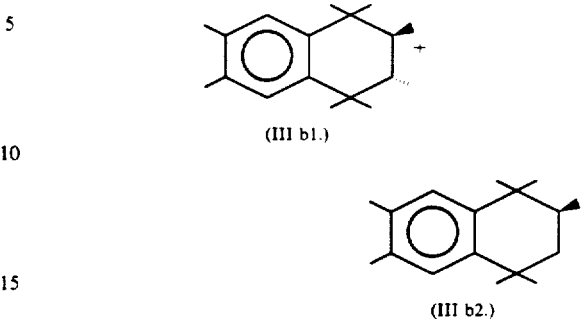

(III b1.)

(III b2.)

The first step in this process consists in a Grignard reaction (hydrometallation) starting from isoprene and pivatoyl chloride (t-BuCOCl, Bu=butyl). This is an original approach which replaces advantageously the Friedel-Crafts acylation generally used to obtain the ketone illustrated in Scheme IV. A classical Friedel-Crafts alkylation follows and, then, reduction by means of LiAlH$_4$. Alternatively, this last step could have been replaced by a hydrogenation reaction. The final step in the process represented is a cyclization which can be carried out under varied conditions. However, the relative proportion of diastereoisomers (III b1.) and (III b2.) in the mixture obtained in this cyclization is strongly dependent on the conditions of the latter. For instance, we discovered that the production of isomer (III b1.) could be favored by the use of polyphosphonic acid (PPA) or P$_2$O$_5$ (see Example 4).

The synthesis represented in Scheme IV makes it possible to prepare symmetrical hydrocarbons wherein the two methyl groups substituting the benzene ring are equivalent, said hydrocarbons being easily oxidized with Ce (IV) to yield a mixture of aldehydes of formula (II) which can be separated by gas chromatography. The mixture of the corresponding ketones can then be obtained by conventional reactions, as is described in Example 6 presented further on.

The Ce (IV) oxidation reaction can actually be applied in a general way to other hydrocarbons of formula (III).

The synthesis of tricyclic compounds of formulae (Ie) to (Ih) was achieved starting from tricyclic hydrocarbons (IIIc) and (IIId). The latter can be prepared by the following processes, which resort to conventional reactions, illustrated below and carried out under the conditions described in detail in the corresponding preparation examples presented later on:

Scheme V (IIIc)

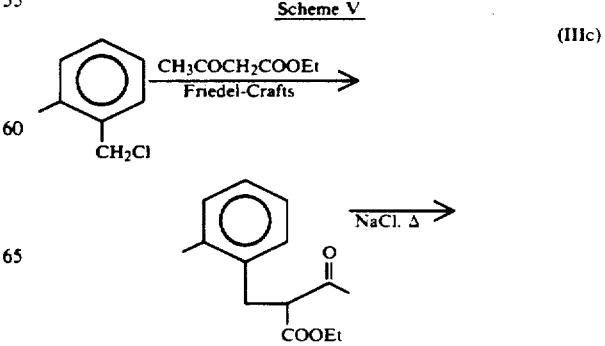

-continued
Scheme V

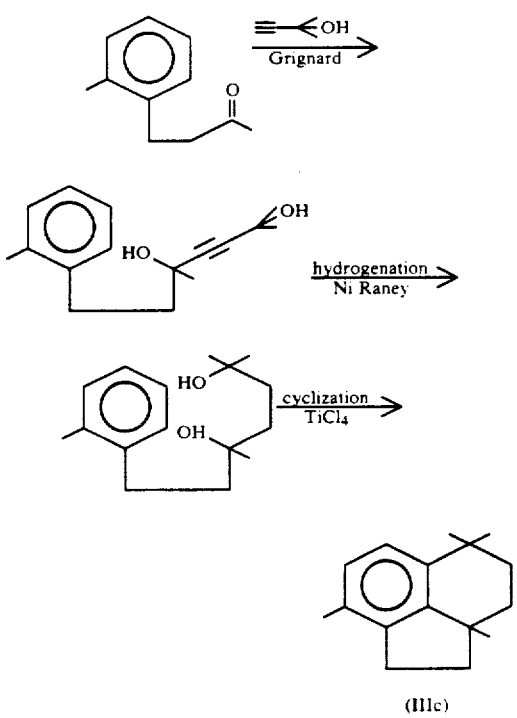

Scheme VI

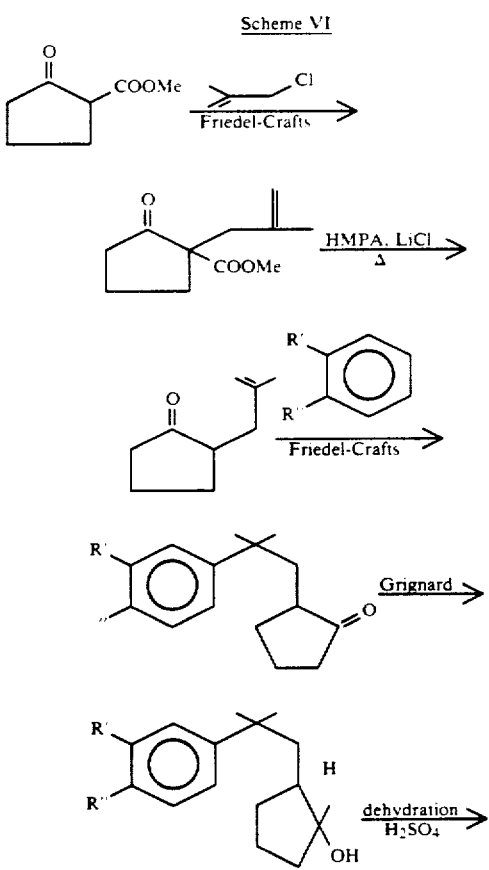

-continued
Scheme VI

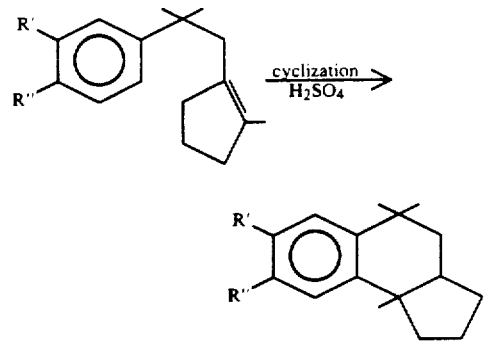

R'=Het R"=$CH_3$, or vice-versa

Hydrocarbon (IIIc) is converted into aldehyde (Ie) and ketone (Ig) by way of Friedel-Crafts acylation reactions. Likewise, mixtures of compounds of formula (If) and (Ih) were obtained starting from the mixture of hydrocarbons (IIId). The specific conditions of these transformations are described in detail in Examples 7 to 10.

The invention will now be described in further detail by way of the following preparation examples, wherein temperatures are indicated in degrees centigrade and the abbreviations have the meaning common in the art.

Moreover, examples of the use of the compounds according to the invention for the preparation of perfuming compositions and perfumed articles are also described in detail. They represent preferential embodiments of the invention, but the latter is not restricted to said examples. In particular, and depending on the desired fragrance effects, compounds of formula (I) other than those cited in the described examples can be used as perfuming ingredients and are capable of imparting to the resulting compositions and articles according to the invention a considerable range of nuanced odor characters of varied strength and tenacity.

EXAMPLE 1

Preparation of
5,6,7,8-tetrahydro-1,3,5,5,8,8-hexamethyl-2-naphthalenecarbaldehyde and of
5,6,7,8-tetrahydro-3,4,5,5,8,8-hexamethyl-2-naphthalenecarbaldehyde a) Preparation of 1,2,3,4-tetrahydro-1,1,4,4,5,6,7-heptamethylnaphthalene In a 3 l three-neck flask, equipped with a mechanical stirrer and kept under nitrogen, 426.0 g of methallyl chloride were slowly (2 h) added to a mixture of 1,2,3-trimethylbenzene (1582.0 g) and $H_2SO_4$ (84.0 g) while the temperature was maintained at 20°. After 3 h, the $H_2SO_4$ was decanted and the organic phase was washed with, in succession, water, an aqueous solution saturated with $NaHCO_3$ and an aqueous solution saturated with NaCl. The excess of 1,2,3-trimethylbenzene (1100.0 g) was recovered through distillation (70°/9.31×$10^3$ to 2.66×$10^3$ Pa) and the residue was distilled (97°-100°/2.66 Pa). A mixture (726.0 g) of two isomers (A/B≃40:60) was obtained which gave the following analytical data and was used as such in the next reaction.

A. 1-(2-chloro-1,1-dimethylethyl)-3,4,5-trimethylbenzene

IR(CDCl$_3$): 2950, 1485, 1390 cm$^{-1}$.

NMR($^1$H,60 MHz): 1.38(s,6H); 2.13(s,3H); 2.27(s,6H); 3.59(s,2H); 7.01(s,2H) δ ppm.

MS: 210(M$^+$,8), 174(7), 161(100), 133(28), 121(34), 115(14), 105(16), 91(19), 77(14).

B. 1-(2-chloro-1,1-dimethylethyl)-2,3,4-trimethylbenzene

IR(CDCl$_3$): 2950, 1485, 1390 cm$^{-1}$.

NMR($^1$H,60 MHz): 1.50(s,6H); 2.17(s,3H); 2.27(s,3H); 2.38(s,3H); 3.82(s,2H); 6.96(d,J=8 Hz,1H); 7.13(d,J=8 Hz,1H) δ ppm.

MS: 210(M$^+$,10), 174(12), 161(100), 133(56), 121(34), 115(19), 105(22), 91(27), 77(19).

In a 1.5 l flask equipped with a mechanical stirrer and kept under nitrogen, a suspension of Mg (41.0 g) in THF (tetrahydrofuran, 100 ml) was heated to reflux. 10 ml of a solution of the mixture of (A+B) prepared above (300.0 g) in THF (100 ml) were then added. Once the reaction had started, more THF was added (300 ml) and then the remaining solution of (A+B) in THF was added over 75 min. The reaction mixture was stirred for 30 min at a temperature of 75°. Methallylchloride (193.0 g) was then added over 20 min, while maintaining the reaction mixture at reflux. During this introduction, MgCl$_2$ was seen to precipitate, the mixture having become heavier, but without hindering the stirring. After 30 min, the mixture was cooled to 10° and hydrolized with water (400 ml). The phases were separated and the aqueous layer was extracted with ether. The combined organic layers were washed with an aqueous solution saturated NaCl, and the solvents were evaporated. Distillation (130°-135°/2.66×10$^2$ Pa) provided 294.0 g (yield 90%) of a colorless oily mixture whose NMR spectrum ($^1$H, 60 MHz) showed a large singlet at 4.65 δ ppm. This mixture was directly used in the following cyclization reaction.

In a 500 ml three-neck flask equipped with mechanical stirring and kept under nitrogen, 288.0 g of the above-mentioned oily mixture were added to a mixture of petroleum ether 30°-50° (100 ml) and H$_2$SO$_4$ (7.0 g), over 1 h and at a temperature of 5°-10°. After 30 min at 10°, the H$_2$SO$_4$ was separated from the organic layer and the latter was washed successively with H$_2$O, saturated NaHCO$_3$ solution and saturated NaCl solution. Recrystallization of the raw product in ethanol (1.1 l) provided 240.0 g (yield 83%) of 1,2,3,4-tetrahydro-1,1,4,4,5,6,7-heptamethylnaphthalene.

M. p. 79°-82°.

IR(CDCl$_3$): 2920, 1455, 1395, 1380 cm$^{-1}$.

NMR($^1$H,60 MHz): 1.27(s,6H); 1.41(s,6H); 1.65(s,4H); 2.12(s,3H); 2.27(s,3H); 2.38(s,3H); 7.01(s,1H) δ ppm.

MS: 230(M$^+$,22), 216(15), 215(100), 174(11), 173(73), 171(14), 159(41), 141(10), 128(10), 57(16).

b) In a flask equipped with a mechanical stirrer, a condenser and a nitrogen inlet, 6.25 g of 1,2,3,4-tetrahydro-1,1,4,4,5,6,7-heptamethylnaphthalene prepared in a) were dissolved in 70 ml of CCl$_4$ and 5.56 g of NBS (N-bromosuccinimide) were added to the solution. The suspension was irradiated with a 100 W lamp to bring the reaction mixture to reflux. After 45 min, the temperature was allowed to return to room temperature and the reaction mixture was poured on H$_2$O and extracted thrice with ether. The combined organic layers were washed with an aqueous solution saturated with NaCl, dried over Na$_2$SO$_4$, filtered and the solvents evaporated.

The raw mixture thus obtained (10.5 g) was composed of the three bromide derivatives of benzene (see Scheme I) and contained about 15% by weight of unreacted starting naphthalene derivative, owing to the fact that the reaction had not been completed in order to avoid the formation of dibromides. This raw mixture was then dissolved in N-methylpyrrolidone (70 ml) and H$_2$O (10 ml) and heated to reflux for 1 h. After cooling to 20°, the reaction mixture was extracted with ether. The organic layer was washed with water three times, then with an aqueous solution saturated with NaCl, dried over Na$_2$SO$_4$ and the solvents were evaporated. 7.65 g of raw product were obtained, which were submitted to column chromatography on SiO$_2$ (200 g), using as elution agent a mixture of cyclohexane/ether 98:2, giving an apolar fraction containing 5,6,7,8-tetrahydro-2,3,5,5,8,8-hexamethyl-1-naphthalenemethanol (1.3 g) and a polar fraction containing isomers 5,6,7,8-tetrahydro-1,3,5,5,8,8-hexamethyl-2-naphthalenemethanol and 5,6,7,8-tetrahydro-3,4,5,5,8,8-hexamethyl-2-naphthalenemethanol (1.86 g, respectively 80:20). The combined yield of these two fractions was 3.16 g (47% in alcohols).

In a 100 ml three-neck flask equipped with a magnetic stirrer, a thermomether and a nitrogen inlet, 2.18 g of PCC (pyridinium chlorochromate) were dissolved in methylene chloride (15 ml) and a solution of the above-mentioned polar fraction (1.55 g, 4:1) in methylene chloride (5 ml) was added dropwise, while maintaining the temperature at 20°. Two hours later, the reaction mixture, which had become dark brown, was filtered on SiO$_2$ (20 g) with CH$_2$Cl$_2$ and the solvent was evaporated. Recrystallization from methanol provided 501 mg of a mixture which contained 5,6,7,8-tetrahydro-1,3,5,5,8,8-hexamethyl-2-naphthalenecarbaldehyde and 5,6,7,8-tetrahydro-3,4,5,5,8,8-hexamethyl-2-naphthalenecarbaldehyde, in a relative portion of 9 to 1, and 439.0 mg of mother liquors (containing 85% of the above-mentioned aldehydes). The yield of the recrystallization fraction and the mother liquor in the above-cited mixture was 57%.

A sample of 5,6,7,8-tetrahydro-3,4,5,5,8,8-hexamethyl-2-naphthalenecarbaldehyde, containing 10% of 5,6,7,8-tetrahydro-1,3,5,5,8,8-hexamethyl-2-naphthalenecarbaldehyde, was obtained by preparative chromatography. The analytical data from these compounds is presented hereinafter.

Treatment of 5,6,7,8-tetrahydro-2,3,5,5,8,8-hexamethyl-1-naphthalenemethanol (1.30 g) with PCC, in an analogous way to that described above, afforded 456.0 m cg of 5,6,7,8-tetrahydro-2,3,5,5,8,8-hexamethyl-1-naphthalenecarbaldehyde (M.p. 74°-80°) and mother liquors (476.0 g, 80% pure), with an estimated yield of 61%. The analytical data from this product is also described hereinafter.

5,6,7,8-tetrahydro-1,3,5,5,8,8-hexamethyl-2-naphthalenecarbaldehyde

IR(CDCl$_3$): 2975, 2940, 2850, 1685, 1600, 1385 cm$^{-1}$.

NMR($^1$H,360 MHz): 1.30(s,6H); 1.45(s,6H); 1.68(broad s,4H); 2.47(s,3H); 2.70(s,3H); 7.07(s,1H); 10.58(s,1H) δ ppm.

MS: 244(M$^+$,50), 229(100), 187(19), 173(22), 159(56), 145(13), 128(10).

Odor note: nicely musky, clearly ambrette (seeds).

5,6,7,8-tetrahydro-3,4,5,5,8,8-hexamethyl-2-naphthalenecarbaldehyde

IR(CDCl$_3$): 2975, 2940, 2850, 1685, 1600, 1385 cm$^{-1}$.

NMR($^1$H,360 MHz): 1.33(s,6H); 1.47(s,6H); 1.68(s,4H); 2.42(s,3H); 2.53(s,3H); 7.67(s,1H); 10.26(s,1H) δ ppm.

MS: 244(M$^+$,50), 229(100), 187(19), 173(22), 159(56), 145(13), 128(10).

Odor note: musky.

5,6,7,8-tetrahydro-2,3,5,5,8,8-hexamethyl-1-naphthalenecarbaldehyde

IR(CDCl$_3$): 2990, 2955, 2890, 1705, 1470, 1380 cm$^{-1}$.

NMR($^1$H,360 MHz): 1.28(s,6H); 1.36(s,6H); 1.61–1.72(m,4H); 2.16(s,3H); 2.26(s,3H); 7.20(s,1H); 10.83(s,1H) δ ppm.

MS: 244(M$^+$,23), 229(100), 211(40), 196(18), 185(15), 169(17), 159(29), 141(17), 128(15), 115(15).

c) 5,6,7,8-tetrahydro-1,3,5,5,8,8-hexamethyl-2-naphthalenecarbaldehyde was also selectively prepared from 1,2,3,4-tetrahydro-1,1,4,4,5,7-hexamethylnaphthalene. The latter was obtained following a preparation method analogous to that described in a), using as starting products m-xylene (490.9 g), methallyl chloride (150.0 g) and H$_2$SO$_4$ (30.0 g), their reaction having yielded 182.8 g (yield 56%) of 1-(2-chloro-1,1-dimethyl)-2,4-dimethylbenzene (containing 10% of its regioisomer). 100.0 g of the latter compound were then treated under the conditions described in a) to yield 97.0 g (yield 88%) of 1-(1,1,4-trimethyl-4-pentenyl)-2,4-dimethylbenzene. The cyclization of the latter product (86.9 g) yielded 80.6 g (yield 93%) of 1,2,3,4-tetrahydro-1,1,4,4,5,7-hexamethylnaphthalene.

B.p.: 120°/2.66×10$^3$ Pa.

IR: 2910, 1600, 1455, 1390, 1375 cm$^{-1}$.

NMR($^1$H,60 MHz): 1.24(s,6H); 1.35(s,6H); 1.66(s,4H); 2.23(s,3H); 6.75(broad s,1H); 7.00(broad s,1H) δ ppm.

MS: 216(M$^+$,33), 201(100), 159(67), 145(29), 141(13), 128(11), 115(10).

A mixture of 1,2,3,4-tetrahydro-1,1,4,4,5,7-hexamethylnaphthalene (5.0 g) of TiCl$_4$ (7.32 g) in methylene chloride (40 ml) was treated with Cl$_2$CHOCH$_3$ (2.66 g) in methylene chloride (5 ml), at 0° and over 20 min. The temperature of the reaction mixture was allowed to reach 20° (20 min) and said mixture was then poured on ice water and extracted with ether. The organic phase was successively washed with a 10% aqueous solution of NaOH, water and an aqueous solution saturated with NaCl, then dried over Na$_2$SO$_4$, evaporated and recrystallized from methanol. 4.06 g (yield 72%) of 5,6,7,8-tetrahydro-1,3,5,5,8,8-hexamethyl-2-naphthalenecarbaldehyde were obtained, the product being identical in data to that described in b).

EXAMPLE 2

Preparation of
5,6,7,8-tetrahydro-1,3,5,5,6,8,8-heptamethyl-2-naphthalenecarbaldehyde and of
5,6,7,8-tetrahydro-3,4,5,5,7,8,8-heptamethyl-2-naphthalenecarbaldehyde a) Preparation of ethyl 3,4-dimethyl-4-pentenoate In a 2 l flask equipped with a mechanical stirrer and kept under nitrogen, a solution of tiglic acid (100.0 g) in sulphuric ether (300 ml) was added to a suspension of LiAlH$_4$ (28.5 g) in ether (300 ml) over 3 h, the temperature having been kept at 5°. The reaction mixture was made to reflux for 1 h and then left under stirring, at room temperature, for one night. After cooling with an ice bath, 100 ml of 5% HCl were added dropwise, followed by 600 ml of 15% HCl and 200 ml of ether to avoid agglomeration. The reaction mixture was extracted with sulphuric ether (3×400 ml) and the combined extracts were washed, in succession, with a saturated solution of NaCl (3×50 ml), 10% Na$_2$CO$_3$ (20 ml) and H$_2$O. The organic phases were collected together, dried over Na$_2$SO$_4$ and evaporated to concentrate (40°/9.7×10$^4$ Pa). The residue (84.8 g) was fractionated in a Vigreux column under normal vacuum to yield 59.3 g (yield 69%) of 2-methyl-2-buten-1-ol.

In a 3 l flask equipped with a mechanical stirrer and a condenser, kept under nitrogen, a mixture of triethylorthoacetate (1117.8 g), propionic acid (2.3 g) and 2-methyl-2-buten-1-ol (59.3 g) was heated at 118° for 72 h in order to distil the ethanol gradually as it was formed. The excess of triethylorthoacetate was recovered and the distillation was completed under reduced pressure. The raw product thus obtained (69.0 g) contained around 80% of the desired pentenoate. Purification on a Fischer column yielded 43.7 g (41%) of ethyl 3,4-dimethyl-4-pentenoate.

b) Preparation of ethyl 3,4-dimethyl-4-(3,4,5-trimethyl-1-phenyl)pentanoate

In a flask equipped with a mechanical stirrer, a thermometer, an introduction ampoule and maintained under nitrogen, 52.0 g of ethyl 3,4-dimethyl-4-pentenoate prepared as in a) were added dropwise, over 1 h, to a suspension of AlCl$_3$ (115.04 g) in 1,2,3-trimethylbenzene (359.99 g), while keeping the temperature at 0°–5°. Once the introduction was completed, the temperature was allowed to increase to 20° and, 15 min later, the reaction mixture was poured on icy water. The mixture was extracted with ether and washed successively with 5% NaOH, water and a NaCl saturated solution. It was then dried over Na$_2$SO$_4$, filtered and the solvents were evaporated. The excess of 1,2,3-trimethylbenzene was distilled at 70°/2.66×10$^3$ Pa. Distillation of the residue at 160°/2.66×10$^2$ Pa provided 70.23 g (yield 76%) of ethyl 3,4-dimethyl-4-(3,4,5-trimethyl-1-phenyl)-pentanoate.

IR: 2970, 1740, 1455, 1380, 1305, 1190 cm$^{-1}$.

NMR($^1$H,60 MHz): 0.85(d,J=7 Hz,3H); 1.23(t,J=7 Hz,3H); 1.23(s,6H); ≃1.80(m,1H); ≃2.20(m,2H); 2.15(s,3H); 2.26(s,6H); 4.06(q,J=7 Hz,2H); 6.93(s,2H) δ ppm.

MS: 276(M$^+$,3), 231(3), 161(100), 147(8), 133(14), 121(13), 105(7), 91(6).

c) Preparation of 2,4,5,5-tetramethyl-5-(3,4,5-trimethyl-1-phenyl)-2-pentanol

A 1.5 l sulfuration flask equipped with a condenser and kept under nitrogen was charged with 15.12 g of Mg which were covered with anhydrous ether (20 ml). The Grignard reaction was triggered by adding 5 to 10 ml of a CH$_3$I (96.56 g) solution in ether (180 ml). As soon as the reaction had started (ether reflux), an ether solution (200 ml) of the pentanoate prepared in b) (69.0 g) was added to the reaction mixture. We continued to add the CH$_3$I solution mentioned above while controlling the ether reflux with a cold water bath (solution added over about 1 h). The mixture was allowed to continue to react for 1 h, the temperature having been kept at 20°, and then carefully hydrolyzed with icy water. It was subsequently extracted with ether, washed with saturated NaCl, dried over Na$_2$SO$_4$, filtered and the solvents were evaporated. 65.1 g (yield ≃100%) of the desired alcohol were obtained and used as such in the following cyclization reaction.

d) Preparation of 1,2,3,4-tetrahydro-1,1,2,4,4,5,6,7-octamethylnaphthalene

A 250 ml three-neck flask equipped with a mechanical stirring and kept under $N_2$, was charged with 100 g of 90% $H_2SO_4$, to which a solution of the raw alcohol obtained in c) (65.1 g) in petroleum ether 80°-100° ($\approx$50 ml) was added dropwise (1 h), while the temperature was kept between 0° and 10°. Once the introduction was completed, the temperature was allowed to increase to 20° and, 30 min later, the $H_2SO_4$ was decanted and ice water was added to the reaction mixture ($\approx$300 ml). The latter was extracted with ether, washed with 10% NaOH and saturated NaCl, dried over $Na_2SO_4$, filtered and evaporated. Recrystallization of the raw product in ethanol afforded 37.3 g of 1,2,3,4-tetrahydro-1,1,2,4,4,5,6,7-octamethylnaphthalene and 18.77 g of mother liquors containing around 55% of this same compound. This compound was used as the starting product in the synthesis of the desired aldehydes.

IR(CDCl$_3$): 2920, 1455, 1385, 1360 cm$^{-1}$.

NMR($^1$H,60 MHz): 0.94(d,J=7 Hz,3H); 1.10(s,3H); 1.25(s,3H); 1.39(s,3H); 1.43(s,3H); 1.60-1.90(m,3H); 2.11(s,3H); 2.23(s,3H); 2.36(s,3H); 7.07(s,1H) $\delta$ ppm.

MS: 244(M$^+$,30), 229(100), 187(92), 173(73), 156(16), 141(17), 128(12), 115(11), 57(13), 41(14).

e) The method described in Example 1b) was followed (Scheme I).

In the halogenation reaction, the following reagents were used: NBS (28.82 g), 1,2,3,4-tetrahydro-1,1,2,4,4,5,6,7-octamethylnaphthalene [prepared in d), 35 g] and CCl$_4$ (350 ml). After the usual treatment, 54.1 g of raw product were obtained, consisting in the mixture of benzyl bromides and unreacted starting octamethylnaphthalene.

This raw product/54.1 g) was used in the hydrolysis reaction with N-methyl-pyrrolidone (300 ml) and H$_2$O (45 ml). After the usual treatment, 44 g of raw product were obtained, containing 5,6,7,8-tetrahydro-3,4,5,5,7,8,8-heptamethyl-2-naphthalenemethanol, 5,6,7,8-tetrahydro-1,3,5,5,6,8,8-heptamethyl-2-naphthalenemethanol and 5,6,7,8-tetrahydro-2,3,5,5,6,8,8-heptamethyl-1-naphthalenemethanol, as well as 15% of unreacted 1,2,3,4-tetrahydro-1,1,2,4,4,5,6,7-octamethylnaphthalene.

This mixture (44.0 g, $\approx$77% weight of alcohols) was used in the oxidation reaction, with PCC (44.9 g) and CH$_2$Cl$_2$ (300 ml). After the filtration, two fractions were obtained, one containing 5.22 g of the above-mentioned octamethylnaphthalene and the other 11.8 g of a mixture composed of 5,6,7,8-tetrahydro-1,3,5,5,6,8,8-heptamethyl-2-naphthalenecarbaldehyde, 5,6,7,8-tetrahydro-3,4,5,5,7,8,8-heptamethyl-2-naphthalenecarbaldehyde, and 5,6,7,8-tetrahydro-2,3,5,5,6,8,8-heptamethyl-1-naphthalenecarbaldehyde, in the respective proportions of 4:5:1 (yield over 3 steps 27%). Preparative chromatography afforded a 9:1 mixture of the first two aldehydes cited.

5,6,7,8-tetrahydro-1,3,5,5,6,8,8-heptamethyl-2-naphthalenecarbaldehyde

IR(CDCl$_3$): 2920, 1680, 1595, 1460, 1370 cm$^{-1}$.

NMR($^1$H,360 MHz): 0.99(d,J=7 Hz,3H); 1.16(s,3H); 1.28(s,3H); 1.35(dd, J=14.2 Hz,1H); 1.42(s,3H); 1.48(s,3H); 1.67(t,J=14 Hz,1H); 1.86(m,1H); 2.49(s,3H); 2.72(s,3H); 7.12(s,1H); 10.61(s,1H) $\delta$ ppm.

MS: 258(M$^+$,35), 245(95), 201(47), 187(60), 173(100), 159(35), 141(20), 128(17), 115(13), 91(13), 57(18), 41(15).

5,6,7,8-tetrahydro-3,4,5,5,7,8,8-heptamethyl-2-naphthalenecarbaldehyde

IR(CDCl$_3$): 2920, 1680, 1595, 1460, 1370 cm$^{-1}$.

NMR($^1$H,360 MHz): 2.43(s,3H); 2.52(s,3H); 7.73(s,1H); 10.61(s,1H) $\delta$ ppm MS: 258(M$^+$,35), 245(95), 201(47), 187(60), 173(100), 159(35), 141(20), 128(17), 115(13), 91(13), 57(18), 41(15).

Odor note: this mixture possessed a nice musky note, clean but slightly weak.

EXAMPLE 3

Preparation of
5,6,7,8-tetrahydro-1,3,5,5,7,8,8-heptamethyl-2-naphthalenecarbaldehyde and
5,6,7,8-tetrahydro-3,4,5,5,6,8,8-heptamethyl-2-naphthalenecarbaldehyde a) Preparation of ethyl 2,4-dimethyl-4-pentenoate In a 3000 ml flask mechanically stirred and equipped with a condenser and a N$_2$ inlet, a solution of sodium ethylate (46.0 g Na, 700 ml absolute ethanol) was prepared and 286.0 g of ethyl acetoacetate added thereto, over 30 min, at a temperature of 15°. The mixture was stirred for 30 min at room temperature and 182.0 g of $\beta$-methallyl chloride were added to it all at once, at the same temperature. Stirring was maintained for 50 h and the mixture was then refluxed for 1 h. The sodium chloride precipitate was filtered and the filtrate was concentrated by solvent evaporation. Ther residue (402.6 g) was fractionated on a Vigreux column, then on a column filled with glass helices topped by a total reflux head. 161.4 g of ethyl 2-acetyl-4-methyl-4-pentenoate were used in the following reaction.

A 2000 ml flask, equipped with mechanical stirring, a condenser and N$_2$ atmosphere, was charged with 24.3 g of Na and 400 ml of ethanol to prepare sodium ethylate. After cooling to 15°, the pentenoate previously prepared (161.4 g) was added to the solution over 30 min, while maintaining the temperature at 15°-20°. 15 g of methyl iodide were added in one go. The exothermic reaction was controlled with an ice bath to keep the temperature at 30° for around 90 min. Stirring was continued during 2 h 30 at 20° and the mixture was then taken to reflux for 4 h. The reaction mixture was left at rest for 56 h and then the NaI precipitate was filtered. 700 ml of toluene were added and the mixture was filtered again. 700 ml of toluene/ethanol azeotrope (rotavapor, 74°/6×10$^4$ Pa) were distilled and 250 ml of the distillate were added to the residue. After cooling to 5°, a new filtration was done. The filtrate was evaporated (74°/2.7×10$^4$ Pa). 240.3 g of raw product were thus obtained, which were purified on a Vigreux column, and then in a glass helix column topped by a total reflux head. 78.1 g of pure ethyl 2-acetyl-2,4-dimethyl-4-pentenoate were thus obtained and this product was used in the following reaction.

b) Preparation of ethyl 2,4-dimethyl-(3,4,5-trimethyl-1-phenyl)pentanoate

The method described in Example 2b) was followed with the reagents cited hereinafter. AlCl$_3$ (125.2 g), 1,2,3-trimethylbenzene (390.9 g), ethyl 2,4-dimethyl-4-pentenoate [prepared in a), 56.5 g]. After usual treatment and distillation, 81.9 g of the desired product were obtained (B.p. 160°/2.7×10$^2$ Pa, yield 82%).

IR: 2950, 1730, 1450, 1370, 1180, 1150 cm$^{-1}$.

NMR($^1$H,60 MHz): 1.02(d,J=7 Hz,3H); 1.14(t,J=7.5 Hz,3H); 1.24(s,6H); $\approx$1.70(m,2H); 2.12(s,3H); 2.27(s,6H); $\approx$3.0-3.5(m,1H); 3.91(q,J=7.5 Hz, 2H); 6.93(s,2H) $\delta$ ppm.

MS: 276(M$^+$,6), 231(5), 187(5), 161(100), 133(11), 121(10), 105(5).

c) Preparation of 2,3,5,5-tetramethyl-5-(3,4,5-trimethyl-1-phenyl)-2-pentanol

We followed the method described in Example 2c), using the following reagents: Mg (17.7 g), MeI (108.9 g), ethyl 2,4-dimethyl-(3,4,5-trimethyl-1-phenyl)pentanoate [prepared according to b), 81.5 g], ether (650 ml). 82.0 g of raw product were obtained and this product was used as such in the cyclization reaction that followed.

d) Preparation of 1,2,3,4-tetrahydro-1,1,2,4,4,6,7,8-octamethylnaphthalene

We followed Example 2d) with the reagents cited hereinafter: raw alcohol prepared in c) (82 g), 90% $H_2SO_4$ (100 g), petroleum ether ($\approx$ 50 ml). After crystallization, 50 g of the desired pure product were obtained and 24.3 g of mother liquors containing around 60% of same product (overall yield 68%). The latter was used as starting product in the synthesis of the desired aldehydes.

IR(CDCl$_3$): 2950, 1450, 1380, 1360 cm$^{-1}$.

NMR($^1$H, 60 MHz): 1.01(d,J=7 Hz,3H); 1.24(s,3H); 1.26(s,3H); 1.33(s,3H); 1.47(s,3H); $\approx$1.70(m,3H); 2.15(s,3H); 2.26(s,3H); 2.41(s,3H); 7.00(s,1H) δ ppm.

MS: 244(M$^+$,30), 229(85), 187(100), 173(58), 157(10).

e) The method described in Example 1b) was followed (Scheme I).

In the halogenation reaction, the following reagents were used: NBS (38.29 g), 1,2,3,4-tetrahydro-1,1,2,4,4,5,6,7-octamethylnaphthalene [prepared in d), 50.0 g], CCl$_4$ (400 ml). After 45 min, the usual treatment was carried out to give 54.2 g of raw product containing the mixture of benzyl bromides and $\approx$15% by weight of unreacted octamethylnaphthalene.

This raw product (54.2 g) was mixed with N-methylpyrrolidone (300 ml) and water (45 ml). The hydrolysis reaction afforded 39.1 g of raw product containing 5,6,7,8-tetrahydro-1,3,5,5,7,8,8-heptamethyl-2-naphthalenemethanol, 5,6,7,8-tetrahydro-3,4,5,5,6,8,8-heptamethyl-2-naphthalenemethanol and 5,6,7,8-tetrahydro-2,3,5,5,7,8,8-heptamethyl-1-naphthalenemethanol, as well as about 15% by weight of unreacted starting octamethylnaphthalene.

The latter raw product (39.1 g, $\approx$83% by weight of alcohols) was used in the oxidation reaction, together with 44.9 g of PCC and 300 ml of CH$_2$Cl$_2$. After filtration, two fractions were obtained, one containing 6.02 g of starting octamethylnaphthalene and the other containing 5.0 g of a mixture of the three aldehydes mentioned above. Gas chromatography allowed the separation of pure 5,6,7,8-tetrahydro-1,3,5,5,7,8,8-heptamethyl-2-naphthalenecarbaldehyde and a sample of 5,6,7,8-tetrahydro-3,4,5,5,6,8,8-heptamethyl-2-naphthalenecarbaldehyde containing 10% by weight of the preceding compound.

IR (mixture,CDCl$_3$): 2950, 2920, 1680, 1580, 1455, 1360 cm$^{-1}$.

5,6,7,8-tetrahydro-1,3,5,5,7,8,8-heptamethyl-2-naphthalenecarbaldehyde

NMR($^1$H,360 MHz): 1.01(d,J=7 Hz,3H); 1.25(s,3H); 1.30(s,3H); 1.35(s,3H); 1.46(s,3H); $\approx$1.40(m,1H); 1.64(t,J=13 Hz,1H); 1.79(m,1H); 2.47(s,3H); 1.32(s,3H); 7.05(s,1H); 10.60(s,1H); δ ppm.

MS: 258(M$^+$,27), 243(38), 201(41), 187(55), 173(100), 159(32), 143(43), 128(25), 115(25), 105(24), 91(35), 77(21), 57(23), 43(24).

5,6,7,8-tetrahydro-3,4,5,5,6,8,8-heptamethyl-2-naphthalenecarbaldehyde

NMR($^1$H,360 MHz): 1.02(d,J=7 Hz,3H); 1.28(s,3H); 1.32(s,3H); 1.35(s,3H); 1.47(s,3H); $\approx$1.40(m,1H); 1.64(t,J=13 Hz,1H); 1.82(m,1H); 2.44(s,3H); 2.54(s,3H); 7.66(s,1H); 10.27(s,1H) δ ppm.

MS: 258(M$^+$,27), 243(38), 201(41), 187(55), 173(100), 159(32), 143(43), 128(25), 115(25), 105(24), 91(35), 77(21), 57(23), 43(24).

Odor note: this mixture presented a very musky, animal, burnt note.

EXAMPLE 4

Preparation of trans-5,6,7,8-tetrahydro-3,5,5,6,7,8,8-heptamethyl-2-naphthalenecarbaldehyde a) Preparation of 2,2,4,5-tetramethyl-5-hexen-3-one A 1 l flask equipped with a mechanical stirrer, a thermometer and a condenser, maintained under nitrogen, was charged at 20° with, successively, recently distilled isoprene (30.0 g), PrMgBr [(Pr=propyl, 1.88 N, 213 ml; prepared from PrBr (Pr=propyl) (54.2 g), Mg (12.7 g) and (CH$_3$CH$_2$)$_2$O (200 ml)], and Cp$_2$TiCl$_2$ (Fluka, 1 g). After 15 h at 20°, the solution was transferred via canula into a cooled 1.5 l flask (−10°) containing pivaloyl chloride (53.0 g) in solution in (CH$_3$CH$_2$)$_2$O (100 ml). After stirring for 1 h, the mixture was poured on saturated NH$_4$Cl, extracted with ether and the organic layers were washed with 5% NaOH, H$_2$O and saturated NaCl. They were then dried over Na$_2$SO$_4$, filtered and evaporated under vacuum. 49.2 g of a yellow liquid were thus obtained. The desired ketone was distilled on a bridge (50°/1.33×10$^3$ Pa). 39.2 g (yield 61%) of 2,2,4,5-tetramethyl-5-hexen-3-one (96% pure).

IR(CDCl$_3$): 3050, 1700, 1640, 1470, 1360, 990 cm$^{-1}$.

NMR($^1$H,60 MHz): 4.80(s,2H); 3.71(q,J=7 Hz,1H); 1.74(broad,3H); 1.17(d, J=7 Hz,3H); 1.12(s,9H) δ ppm.

MS: 154(M$^+$,3), 85(32), 69(14), 57(100), 41(34).

b) Preparation of 5-(3,4-dimethyl-1-phenyl)-2,2,4,5-tetramethyl-3-hexanone

A solution of the ketone prepared in a) (37.2 g) in o-xylene (50 ml) was added dropwise to a suspension of AlCl$_3$ (36.2 g) in o-xylene (380 ml) over 1 h while maintaining the temperature at 0°. The temperature was allowed to increase to 10° (around 30 min) and the reaction mixture was poured on H$_2$O, extracted with ether and washed with Na$_2$CO$_3$, then saturated NaCl. After drying over Na$_2$SO$_4$ and concentrating by distillation on a bridge, 54.4 g of the desired ketone were obtained (97% pure, yield 88%).

B. p.$\approx$120°/1.33×10$^2$ Pa.

IR(CDCl$_3$): 2950, 1690, 1470, 1360, 990 cm$^{-1}$.

NMR($^1$H,60 MHz): 7.05(broad,3H); 3.27(q,J=7 Hz,1H); 2.26(s,3H); 2.22(s,3H); 1.46(s,3H); 1.37(s,3H); 0.96(s,9H); 0.95(d,J=7 Hz,3H) δ ppm.

MS: 260(M$^+$,1), 147(100), 131(8), 119(17), 91(10), 57(12), 41(10).

c) Preparation of 5-(3,4-dimethyl-1-phenyl)-2,2,4,5-tetramethyl-3-hexanol

In a 1 l flask equipped with mechanical stirring, a thermometer and a condenser, maintained under nitrogen, a solution of the ketone prepared in b) (54.4 g) in (CH$_3$CH$_2$)$_2$O (50 ml) was added to a suspension of LiAlH$_4$ (3.80 g) in (CH$_3$CH$_2$)$_2$O (250 ml). After cooling to 10°, 4 ml of water were carefully added dropwise, then 4 ml of 5% NaOH and 12 ml of water. The resulting alcohol was filtered, concentrated and distilled (bridge: 130°-140°/2.0×10$^2$ Pa). 31.5 g of the desired product were obtained (98% pure; yield 97%; mixture of diastereomers 94:6).

IR: 3600, 2980, 1840, 1370, 1010 cm$^{-1}$.

NMR($^1$H,360 MHz+D$_2$O): 7.18(s,1H); 7.14(broad d,J=7.5 Hz,1H); 7.07(d,J=7.5 Hz,1H); 3.09(d,J=7.5 Hz,1H); 2.04(s,3H); 2.02(s,3H); 2.01(q,J=7 Hz,1H); 1.46(s,3H); 1.20(s,3H); 1.05(d,J=7 Hz,3H); 0.81(s,9H) δ ppm.

MS: 244(trace,M$^+$,18), 187(7), 173(7), 147(100), 131(8), 119(17), 107(9), 91(10), 57(8), 41(13).

d) Preparation of trans-1,2,3,4-tetrahydro-1,1,2,3,4,4,6,7-octamethylnaphthalene and cis-1,2,3,4-tetrahydro-1,1,2,3,4,4,6,7-octamethylnaphthalene The alcohol prepared under c) (41.6 g) was added under stirring and external cooling to a mixture of methanesulphonic acid (21.25 g) and P$_2$O$_5$ (8.5 g). The temperature was kept at 40° for 4 h. The reaction mixture was cooled, rendered more fluid by adding CH$_2$Cl$_2$ (10 ml) and transferred into a 1 l beaker containing an ice-water mixture. The hydrocarbon formed in the reaction was extracted with ether, washed with 5% NaOH, H$_2$O, then saturated NaCl, dried over Na$_2$SO$_4$ and concentrated. 37.3 g of raw product, containing a mixture of trans- and cis-isomers in the respective proportions of 3:1, were obtained. Crystallization from ethanol, distillation of the mother liquors (110°/1.33×10$^2$ Pa) and crystallization of the distilled fractions provided 16.7 g of the desired trans-isomer (98% pure, yield 43%) and an oil containing a mixture of trans- and cis-isomers (19.8 g, ≃56% pure, trans/cis ≃40:60). Residues: 0.52 g.

trans-1,2,3,4-tetrahydro-1,1,2,3,4,4,6,7-octamethylnaphthalene

IR(CHCl$_3$): 2990, 1500, 1450, 1400, 1370 cm$^{-1}$.

NMR($^1$H,360 MHz): 7.12(s,2H); 2.23(s,6H); 1.58(m,2H); 1.31(s,6H); 1.09(s,6H); 0.96(d,J=6 Hz,6H) δ ppm.

NMR($^{13}$C,360 MHz): 143.1(s); 133.6(s); 128.2(d); 39.5(d); 37.5(s); 29.6(q); 25.7(q); 19.5(q); 13.9(q) δ ppm.

MS: 244(M$^-$,7), 229(24), 187(43), 173(100), 157(12), 145(23), 128(11), 91(8) 57(38), 41(9).

cis-1,2,3,4-tetrahydro-1,1,2,3,4,4,6,7-octamethylnaphthalene

IR(CHCl$_3$): 2990, 1500, 1450, 1400, 1370 cm$^{-1}$.

NMR($^1$H,360 MHz): 7.08(s,2H); 2.23(s,6H); 1.88(broad q,2H); 1.26(s,6H); 1.25(s,6H); 0.95(d,J=7 Hz,6H) δ ppm.

NMR($^{13}$C,360 MHz): 142.0(s); 133.6(s); 127.9(d); 41.4(d); 37.1(s); 33.7(q); 27.7(q); 19.4(q); 13.3(q) δ ppm.

MS: 244(M$^+$,7), 229(24), 187(43), 173(100), 157(12), 145(23), 128(11), 91(8) 57(38), 41(9).

e) To a solution of trans-1,2,3,4-tetrahydro-1,1,2,3,4,4,6,7-octamethylnaphthalene [obtained in d), 16.0 g] in methanol (700 ml) were added 16 portions of Ce(NH$_4$)$_2$(NO$_3$)$_6$ (16×16.0 g=256.0 g) in methanol (16×100 ml), over 8 h, while maintaining the temperature at 50°. Around ⅔ of the methanol were evaporated and the resulting product was extracted with petroleum ether 30°-50°/sat NaCl. The raw product thus obtained (19.1 g) contained a new, heavier product which was not identified. After crystallizing in ethanol, treating the mother liquors and recrystallizing, 12.1 g of the desired trans-5,6,7,8-tetrahydro-3,5,5,6,7,8,8-heptamethyl-2-naphthalenecarbaldehyde (98.5% pure, yield 80%) were obtained.

IR(CDCl$_3$): 2960, 1680, 1600, 1450, 1360, 1205 cm$^{-1}$.

NMR($^1$H,360 MHz): 10.19(s,1H); 7.80(s,1H); 7.21(s,1H); 2.61(s,3H); 1.59(m,2H); 1.35(s,3H); 1.33(s,3H); 1.12(s,6H); 0.99(d,J=6 Hz,6H) δ ppm.

MS: 258(M$^+$,24), 243(58), 201(30), 187(100), 173(40), 159(34), 141(18), 131(23), 115(15), 57(12), 43(47).

Odor note: described in the introduction of this specification.

EXAMPLE 5

Preparation of cis-5,6,7,8-tetrahydro-3,5,5,6,7,8,8-heptamethyl-2-naphthalenecarbaldehyde This product, which is a diastereomer of the compound prepared in Example 4, was obtained via oxidation of a mixture containing the two hydrocarbon isomers prepared according to Example 4d), followed by preparative chromatography.

IR(CDCl$_3$): 2960, 1680, 1600, 1450, 1360, 1205 cm$^{-1}$.

NMR($^1$H,360 MHz); 10.20(s,1H); 7.76(s,1H); 71.8(s,1H); 2.62(s,3H); 1.92(m,2H); 1.32(s,3H); 1.31(s,3H); 1.28(2s,6H); 0.95(d,J=7 Hz,6H) δ ppm.

NMR($^{13}$C): 192.7(d); 151.3(s); 143.0(s); 137.2(s); 132.2(s); 131.3(d); 130.2(d); 41.1(d); 41.1(d); 38.0(s); 37.4(s); 33.7(q); 33.4(q); 27.6(q); 27.4(q); 19.2(q); 13.2(q); 13.2(q); δ ppm.

MS: 258(M$^+$,24), 243(58), 201(30), 187(100), 173(40), 159(34), 141(18), 131(23), 115(15), 57(12), 43(47).

Odor note: musky, earthy, slightly animal.

EXAMPLE 6

Preparation of trans-(5,6,7,8-tetrahydro-3,5,5,6,7,8,8-heptamethyl-2-naphthyl)-1-ethanone A solution of CH$_3$MgCl/THF (9.7 ml, 3.54N) was added to a solution, in THF (40 ml), of the aldehyde prepared in example 4 (7.0 g), while keeping the temperature at 20° (ice bath). The reaction mixture was hydrolized with NH$_4$Cl, extracted with ether and washed with H$_2$O and saturated NaCl. It was then dried over Na$_2$SO$_4$ and concentrated. 6.9 g of raw product were obtained. A solution of 6.26 g of this product in CH$_2$Cl$_2$ (60 ml) was added dropwise to a solution of PCC (7.86 g) in CH$_2$Cl$_2$ (20 ml). The mixture was stirred for 2 h keeping the temperature at 20°, filtered over SiO$_2$ under a slight pressure of nitrogen, concentrated (5.86 g) and crystallized in ethanol. The mother liquors were chromatographed (SiO$_2$, CH$_2$Cl$_2$) and crystallized. A total amount of 4.3 g of trans-(5,6,7,8-tetrahydro-3,5,5,6,7,8,8-heptamethyl-2-naphthyl)-1-ethanone (95% pure, yield 62%) was obtained.

IR(CDCl$_3$): 2960, 1670, 1440, 1350, 1220 cm$^{-1}$.

NMR ($^1$H,360 MHz,CDCl$_3$): 7.73(s,1H); 7.20(s,1H); 2.45(s,3H); 2.40(s,3H); 1.58(m,2H); 1.30(s,6H); 1.06(s,6H); 0.91(d,J=6.5 Hz,6H); δ ppm.

MS: 272(M$^+$,7), 257(22), 215(14), 201(40), 173(23), 159(16), 141(16), 128(17), 115(12), 57(13), 41(100).

Odor note: described in the introduction to this specification.

EXAMPLE 7

Preparation of 1,2,6,7,8,8a-hexahydro-3,6,6,8a-tetramethyl-4-acenaphthylcarbaldehyde a) Preparation of ethyl 2-acetyl-3-(2-methyl-1-phenyl)propanoate In a 2.5 l flask equipped with a mechanical stirrer, a condenser, a thermometer and a nitrogen inlet, α-chloro-o-xylene (Fluka, 140.6 g) was mixed with ethyl acetoacetate (130 g), a fine powder of potassium carbonate (414 g) and 800 ml of toluene. The mixture was heated to 100° for 20 h. After cooling, H$_2$O was added (500 ml). The organic phase was washed with water and saturated NaCl, then dried over Na$_2$SO$_4$ and evaporated. 269.6 g of a brown oil were obtained which was distilled (120°-125°/5.65 Pa) to yield 163 g of ethyl 2-acetyl-3-(2-methyl-1-phenyl)propanoate (98% pure, yield 70%).

b) Preparation of 4-(2-methyl-1-phenyl)-2-butanone

An autoclave of 1 l was charged with 161.5 g of ethyl 2-acetyl-3-(2-methyl-1-phenyl)propanoate obtained in a), 16.4 g of NaCl, 150 ml of DMSO and 25 ml of H$_2$O. The mixture was heated to 160° for 7 h. The cooled reaction mixture was extracted with petroleum ether 30°-50°, washed 5 times with a saturated solution of NaCl, dried over Na$_2$SO$_4$, filtered and evaporated. Distillation of the obtained raw product (13.3 Pa) provided 101 g of the desired butanone (98% pure, yield 91%).

P.Eb. 65°-70°/13.3 Pa.

IR: 2925, 1705, 1490, 1350, 1160 cm$^{-1}$.

NMR($^1$H,60 MHz): 2.10(s,3H); 2.28(s,3H); 2.65-3.00(m,4H); 7.07(s,4H) δ ppm.

MS: 162(M$^+$,2), 144(100), 129(50), 119(52), 105(83), 91(45), 77(28), 65(18), 43(58).

c) Preparation of 7-(2-methyl-1-phenyl)-2,5-dimethyl-hept-3-yne-2,5-diol

In a 1 l flask 2-methyl-3-butyn-2-ol (47 g) was added to a solution of EtMgBr (1.12 mol of Mg and 1.12 mol of ethyl bromide in 200 ml of anhydrous ether at reflux) over 30 min while keeping the temperature at 0°-5°. The heterogeneous mixture was heated to 20° for 30 min, under stirring, and then to reflux for 1 h. 69.7 g of 4-(2-methyl-1-phenyl)-2-butanone prepared according to b) were added and the reaction mixture was heated to reflux for 1 h. The mixture, by then homogeneous, was hydrolized with an aqueous solution saturated with NH$_4$Cl and ice, extracted with ether, washed with saturated NaCl, dried and evaporated. 107.9 g (yield ≈ 100%) of a yellow oil, consisting of the desired diol, were obtained.

IR: 3350 cm$^{-1}$.

NMR($^1$H,60 MHz): 1.50(s,9H); 1.70-2.03(m,2H); 2.30(s,3H); 2.63-2.94(m,2H); 2.94(broad s,2H); 7.13(s,4H) δ ppm.

d) Preparation of 7-(2-methyl-1-phenyl)-2,5-dimethylheptane-2,5-diol 60 g of the diol prepared in c) were hydrogenated in an autoclave, at 70° and 50 H$_2$ atmospheres, in the presence of about 3.0 g of Raney-Ni in methanol (80 ml). After 4 days under the same conditions, the suspension was filtered and the filtrate evaporated to obtain 60 g of 7-(2-methyl-1-phenyl)-2,5-dimethylheptane-2,5-diol (yield ≈ 100%).

IR: 3350, 2930, 1455, 1370 cm$^{-1}$.

NMR($^1$H,60 MHz): 1.22(2s,9H); 1.60(s,4H); 1.50-1.90(m,2H); 2.22(broad s, 2H,exchange with D$_2$O); 2.30(s,3H); 2.45-2.85(m,2H); 7.12(s,4H) δ ppm.

e) Preparation of 1,2,2a,3,4,5-hexahydro-2a,5,5,8-tetramethylacenaphthene

A stirred and cooled (4°) solution of the diol prepared in d) (12.5 g) in 1,2-dichloroethane (150 ml) was treated dropwise with TiCl$_4$ (16.5 ml). After stirring for 30 min, an aqueous solution saturated with NaCl (50 ml) was added dropwise, the temperature rising to 30°. The mixture was washed with an aqueous solution saturated with NaHCO$_3$, then with an aqueous solution saturated with NaCl, dried over Na$_2$SO$_4$, evaporated and distilled (130°/2.66 Pa). 7.76 g of the desired product were thus obtained (yield 77%).

IR: 2920, 1485, 1445, 1360 cm$^{-1}$.

NMR($^1$H,360 MHz) : 1.12(2s,6H) ; 1.38(s,3H); 1.60-1.85(m,4H); 2.02(m,2H); 2.22(s,3H); 2.68(m,1H); 2.97(m,1H); 6.94(d,J=8 Hz,1H); 7.01(d, J=8 Hz,1H) δ ppm.

MS: 214(M$^+$,15), 199(100), 157(18), 143(14).

f) The precursor 1,2,2a,3,4,5-hexahydro-2a,5,5,8-tetramethylacenaphthene obtained according to e) was treated in a way similar to that described in example 1c), with TiCl$_4$ and Cl$_2$CHOCH$_3$. 4.71 g of said precursor were used in the acylation reaction and 3.14 g of 1,2,6,7,8,8a-hexahydro-3,6,6,8a-tetramethyl-4-acenaphthylenecarbaldehyde (yield 59%).

IR(CDCl$_3$): 2950, 2855, 1680, 1590, 1450 cm$^{-1}$.

NMR($^1$H,60 MHz): 1.15(s,6H); 1.41(s,3H); 1.65-2.30(m,6H); 2.52(s,3H); 2.70-3.15(m,2H); 7.60(s,1H); 10.23(s,1H) δ ppm.

MS: 242(M$^+$,18), 227(100), 199(20), 165(10), 157(36), 143(25), 128(17), 115(14), 92(12), 69(11).

Odor note: nicely musky with a relatively weak musk-ambrette side

EXAMPLE 8

Preparation of (1,2,6,7,8,8a-hexahydro-3,6,6,8a-tetramethyl-4-acenaphthylenyl)-1-ethanone A solution of the hydrocarbon prepared in example 7e) (1.28 g) in 1,2-dichloroethane was added dropwise to a suspension of AlCl$_3$ (960 mg) in 1,2-dichloroethane (10 ml). To the orange suspension 518 g of acetyl chloride were added. After 30 min, water was added and the reaction product was extracted with ether. The organic phase was washed with a saturated solution of NaHCO$_3$, then with a saturated solution of NaCl, dried over Na$_2$SO$_4$, evaporated and purified by column chromatography (SiO$_2$, cyclohexane/ethyl acetate 95:5). 0.80 g of the desired ketone were obtained (yield 52%).

IR(CHCl$_3$): 2920, 2850, 1675, 1445, 1345, 1290, 1245 cm$^{-1}$.

NMR($^1$H,360 MHz): 1.13(s,3H); 1.15(s,3H); 1.40(s,3H); 1.58-1.85(m,4H); 1.98-2.09(m,2H); 2.37(s,3H); 2.56(s,3H); 2.74(m,1H); 2.99(m,1H); 7.43(s,1H) δ ppm.

MS: 256(M$^+$,11), 241(87), 199(20), 153(10), 43(100).

Odor note: musky with a character typical of the nitro-aromatic musky compounds.

EXAMPLE 9

Preparation of a mixture of 2,3,3a,4,5,9b-hexahydro-5,5,8,9b-tetramethyl-1H-benz[e]indene-7-carbaldehyde and 2,3,3a,4,5,9b-hexahydro-5,5,7,9b-tetramethyl-1H-benz[e]indene-8-carbaldehyde a) Preparation of methyl 1-(2-methyl-2-propenyl)-2-oxo-1-cyclopentanecarboxylate A mixture of methyl 1-cyclopentanone-2-carboxylate (Fluka, 106.5 g), methallyl chloride (88 ml), K$_2$CO$_3$ (207 g) and acetone (500 ml) was heated to reflux for 2 h. More methallyl chloride (44 ml) was added and the mixture was refluxed for 20 h. The white reaction mass was dissolved in water and the product extracted with ether. Washing (3% aqueous NaOH) and the usual treatment provided 148 g of an oil which was submitted to a fractional distillation to give 113 g of the desired keto-ester (yield 77%, B.p. 105°–107°/5.32×10² Pa).

IR: 2950, 1750, 1720, 1430, 1210 cm⁻¹.

NMR(¹H,60 MHz): 1.64(s,3H); 1.70–3.00(m,8H); 3.68(s,3H); 4.73(broad s,1H); 4.85(broad s,1H) δ ppm.

MS: 178(M⁺,16), 168(16), 140(45), 136(30), 121(36), 109(100), 93(35), 79(60), 67(36), 55(41), 39(33).

b) Preparation of 2-(2-methyl-2-propenyl)-1-cyclopentanone

A mixture of the keto-ester prepared in a) (78.4 g), HMPA (hexamethylphosphoramide, 250 ml) and LiCl (34 g) was heated to 73° for 36 h. Extraction (3 times, ether/water) of the reaction product provided 70.3 g of a brown oil which was submitted to fractional distillation to give 34.7 g of the above-mentioned ketone (yield 62%, B.p. 63°–75°/5.32×10² Pa).

NMR(¹H,60 MHz): 1.71(s,3H); ≈1.50–2.70(m,9H); 4.68(broad s,2H) δ ppm.

MS: 138(M⁺,45), 123(12), 110(38), 95(37), 82(100), 67(77), 55(38), 41(35).

c) Preparation of a mixture of 2-[2-methyl-2-(4-methyl-1-phenyl)propyl]-1-cyclopentanone and 2-[2-methyl-2-(3-methyl-1-phenyl)propyl]-1-cyclopentanone 10.35 g of the ketone prepared in b) were added dropwise to a suspension of AlCl₃ (15 g) in toluene (138 g) at −20°. The temperature was allowed to raise to 10° and the reaction mixture was stirred for 30 min, hydrolized with water and extracted with ether. Part (6 g) of the yellow oil thus obtained (16.56 g, yield 95%) was distilled in a bulb-to-bulb apparatus (130°/1.33 Pa) to give 5.2 g of a 3:1 mixture of the above-cited ketones (yield 83%).

IR: 2950, 1735, 1510, 1450, 1150 cm⁻¹.

NMR(¹H,60 MHz,characteristic peaks): 1.28(s,6H); 2.30(large s,3H); 6.90–7.30(m,4H) δ ppm.

MS: 133(M⁺,100), 105(25), 91(10), 41(12).

d) Preparation of a mixture of 1-methyl-2-[2-methyl-2-(4-methyl-1-phenyl)propyl]-1-cyclopentanol and 1-methyl-2-[2-methyl-2-(3-methyl-1-phenyl)propyl]-1-cyclopentanol A solution of CH₃MgI (prepared with 3.4 ml of CH₃I and 1.2 g of Mg) in ether (100 ml) was treated at 20° with a solution of the raw mixture of ketones obtained in c) (10.44 g) in ether (10 ml). Once the addition was completed (about 10 min), the resulting mixture of alcohols was hydrolized and extracted with ether. It was then used as such in the following preparation step.

e) Preparation of a mixture of 1-[1,1-dimethyl-2-(2-methyl-1-cyclopenten-1-yl)ethyl]-4-methylbenzene and 1-[1,1-dimethyl-2-(2-methyl-1-cyclopenten-1-yl)ethyl]-3-methylbenzene A solution of the raw alcohol mixture obtained in d) (9.84 g), petroleum ether 30°–50° (150 ml) and 98% H₂SO₄ (0.75 ml) was stirred for 1 h while keeping the temperature at 20°. The reaction mixture was extracted and bulb-to-bulb distilled (130°/5.65 Pa) to give 6.89 g of a mixture containing the above-mentioned olefins.

NMR(¹H,60 MHz,characteristic peaks): 1.25(s,6H); 1.54(broad s,3H); 2.29(broad s,3H); 6.88–7.30(m,4H) δ ppm.

f) Preparation of a mixture of 1,2,3,3a,4,5-hexahydro-1a,5,5,8-tetramethylacenaphthylene and 1,2,3,3a,4,5-hexahydro-1a,5,5,7-tetramethylacenaphthylene A solution of olefine mixture obtained in e) (5.5 g), petroleum ether 30°–50° (120 ml) and 98% H2SO4 (0.5 ml) was heated to reflux (50°) for 5 h. Extraction and bulb-to-bulb distillation (140°/13.3 Pa) provided a mixture of the above-mentioned hydrocarbons.

NMR(¹H,60 MHz,characteristic peaks): 1.20–1.30(4s,9H); 2.30(s,3H); 6.80–7.30(m,3H) δ ppm.

g) The acylation reaction of the hydrocarbons prepared in f) was carried out as described in Example 1c) using TiCl₄ (1.86 ml) in methylene chloride (30 ml) and Cl₂CHOCH₃ (0.8 ml) in methylene chloride (5 ml). 1.05 g of a mixture of the isomers 2,3,3a,4,5,9b-hexahydro-5,5,8,9b-tetramethyl-1H-benz[e]indene-7-carbaldehyde and 2,3,3a,4,5,9b-hexahydro-5,5,7,9b-tetramethyl-1H-benz[e]inde, in the relative proportions of 3:1, was obtained (yield 45%).

IR: 2940, 2850, 1680, 1600, 1540, 1440, 1205 cm⁻¹.

NMR(¹H,60 MHz): 1.22–1.42(4s,9H); 1.40–2.30(m,9H); 2.62(s,3H); 7.10(7.17\*)(s,1H); 7.70(7.64\*)(s,1H); 10.14(s,1H) δ ppm.

\* minor isomer's peaks

MS: major isomer—256(M⁺,29), 241(100), 199(11), 185(45), 171(58), 157(45), 143(28), 128(22), 69(24).

MS: minor isomer—256(M⁺,57), 241(100), 227(37), 214(23), 199(27), 185(57), 171(100), 157(57), 143(38), 128(35), 115(23), 69(28), 55(26), 41(28).

Odor note: musky, floral.

EXAMPLE 10

Preparation of a mixture of
1-(2,3,3a,4,5,9b-hexahydro-5,5,8,9b-tetramethyl-1H-benz[e]indene-7-yl)-1-ethanone and
1-(2,3,3a,4,5,9b-hexahydro-5,5,7,9b-tetramethyl-1H-benz[e]inden-8-yl)-1-ethanone This ketone mixture was obtained from the hydrocarbon mixture prepared in Example 9f) and following a method analogous to that described in Example 8. A mixture of the isomeric ketones above-mentioned (0.45 g) in the relative proportions of 3:1, was obtained.

NMR(¹H,60 MHz): 1.19–1.34(5s,9H); 1.40–2.30(m,9H); 2.49 and 2.53(2s,+2 shoulders,6H); 7.03(7.06\*)(s,1H); 7.60(7.53\*)(s,1H) δ ppm.

minor isomer's peaks

MS: 270(M⁺,13), 255(43), 213(8), 199(8), 185(8), 171(7), 153(8), 141(8), 128(10), 115(10), 91(8), 43(100).

Odor note: musky, fruity.

EXAMPLE 11

Base Composition of the Floral Type for a Powder Detergent

A base composition of the floral type, intended for a powder detergent, was prepared with the following ingredients:

| Ingredients | Parts by weight |
|---|---|
| Dimethylbenzylcarbinyl acetate | 100 |
| Hexylcinnamic aldehyde | 2500 |
| 10%\* AMBROX ® DL¹⁾ | 50 |
| Isononyl acetate | 250 |
| Verdyl propionate | 800 |
| Coumarine | 100 |
| Cyclamen aldehyde | 350 |
| p-tert-Butylcyclohexanol acetate | 1100 |
| FLEURAMONE ®²⁾ | 200 |
| ISORALDEINE ® 70³⁾ | 300 |
| LILIAL ®⁴⁾ | 800 |
| Phenylethyl alcohol | 800 |
| Benzyle salicylate | 400 |
| Tetrahydrolinalol | 400 |
| VERDOX ®⁵⁾ | 250 |
| VERTOFIX COEUR ®⁶⁾ | 500 |

| Ingredients | Parts by weight |
|---|---|
| Total | 9000 |

*in dipropyleneglycol (DIPG)
[1] tetramethyl perhydronaphthofuran; origin: Firmenich SA, Geneva
[2] 2-heptyl-1-cyclopentanone; origin: International Flavors and Fragrances Inc.
[3] iso-methylionone; origin: L. Givaudan SA, Geneva
[4] 3-(4-tert-butyl-1-phenyl-2-methyl)propanal; origin: L. Givaudan SA, Geneva
[5] 2-tert-butyl-1-cyclohexyl acetate; origin: International Flavors and Fragrances Inc.
[6] origin: International Flavors and Fragrances Inc.

Four perfuming compositions were prepared with this base composition and the following ingredients (parts by weight):

|  | A | B | C | D |
|---|---|---|---|---|
| Base composition | 9000 | 9000 | 9000 | 9000 |
| trans-5,6,7,8-tetrahydro-3,5,5,6,7,8,8-heptamethyl-2-naphthalenecarbaldehyde | 500 | 250 | — | — |
| trans-(5,6,7,8-tetrahydro-3,5,5,6,7,8,8-heptamethyl-2-naphthyl)-1-ethanone | — | — | 1000 | — |
| TONALID ®* | — | — | — | 1000 |
| Dipropyleneglycol | 500 | 750 | — | — |
| Total | 10000 | 10000 | 10000 | 10000 |

*7-acetyl-1,1,3,4,4,6-hexamethyltetralin; origin: Polak's Frutal Works

These varied compositions were evaluated for comparison by a panel of expert perfumers who judged that composition A developed an overdosed, very powerful, musky-animal odor note. Composition B, whose concentration in trans-5,6,7,8-tetrahydro-3,5,5,6,7,8,8-heptamethyl-2-naphthalenecarbaldehyde was half that of composition A, was judged more balanced than the latter but still very musky-animal. Comparing composition B with composition D, it became evident that the first possessed a very different odor character from the second and that its amber-animal note was very perceptible. As for composition C, it was found that it was closer to composition D, as a result of its more floral musky effect, sweeter than those of compositions A and B. The character of composition C was nevertheless different from that of composition D.

These perfuming compositions were added to 4 samples of a powder detergent which were then used in the washing of linen articles. The latter were dried in the open air for 24 h. The differences cited above between the odor effects of the varied compositions were even more obvious when the various linen batches, treated with the 4 detergent samples, were compared with each other. In addition, the strength of composition B was even more accentuated relative to that of composition D, and its substantivity was also better.

EXAMPLE 12

Base Composition for a Masculine Lotion

A base perfuming composition, intended for a masculine lotion, was prepared by admixture of the following ingredients:

| Ingredients | Parts by weight |
|---|---|
| 10%* Geranyl acetate | 150 |
| Lynalyl acetate | 200 |
| 1%* γ-Undecalactone | 100 |
| Bergamot | 1500 |
| Lemon oil | 150 |
| Coumarine | 125 |
| Dihydromyrcenol[1] | 200 |
| FLOROL ®[2] | 50 |
| 10%* Purified indol | 75 |
| Iso E Super[3] | 2000 |
| 10%* Isobutylquinolein[4] | 25 |
| LYRAL ®[5] | 600 |
| Mandarin oil | 700 |
| 10%* Crystal moss | 350 |
| Nutmeg | 100 |
| HEDIONE ®[6] | 350 |
| 10%* Methyl octin carbonate | 850 |
| Patchouli | 200 |
| Amyl salicylate | 200 |
| SANDELA ®[7] | 350 |
| VERTOFIX COEUR ®[8] | 1150 |
| 10%* β-Ionone | 100 |
| 10%* Cyclal C[9] | 75 |
| TIMBEROL ®[10] | 150 |
| Total | 9750 |

*in DIPG
[1] origin: International Flavors & Fragrances Inc.
[2] 4-methyl-2-methylpropyl-4-2H-pyranol; origin: Firmenich SA, Geneva
[3] 2-acetyl-1,2,3,4,5,6,7,8-octahydro-2,3,8,8-tetramethylnaphthalene; origin: International Flavors & Fragrances Inc.
[4] 6-(1-methylpropyl)quinolein); origin: Flavors & Fragrances Inc.
[5] 4-(4-hydroxy-4-methylpentyl)-3-cyclohexen-1-carboxaldehyde; origin: International Flavors and Fragrances Inc.
[6] methyl dihydrojasmonate; origin: L. Givaudan SA, Geneva
[7] 3-(isocamphyl-5)-cyclohexan-1-ol; origin: L. Givaudan SA, Geneva
[8] see Example 11
[9] 3,5-dimethyl-3-cyclohexen-1-carbaldehyde; origin: L. Givaudan SA, Geneva
[10] 1-(2,2,6-trimethylcyclohexyl)-3-hexanol; origin: Dragoco AG., RFA 250 Parts by weight of trans-5,6,7,8-tetrahydro-3,5,5,6,7,8,8-heptamethyl-2-naphthalenecarbaldehyde were added to this base composition. A new composition was thus obtained whose odor note had been entirely changed. Apart from the very obvious amber-animal effect felt at the beginning, the mixture had improved in volume and strength and the musky effect had become clearly perceptible. The lotion had thus acquired a more masculine connotation. These effects became even more marked and evident when the smelling strips were newly scented 24 h later.

What we claim is:

1. A method to improve, enhance or modify the odor properties of a perfuming composition or perfumed article, which method comprises adding to said composition or article an odor effective amount of a compound of formula

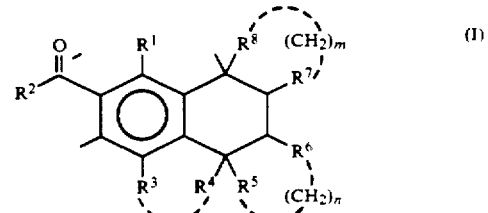

wherein
a) indexes m and n are identical and stand each for an integer number equal to zero, symbols $R^1$ and $R^2$ are identical and represent each a hydrogen atom, or are different and represent each a hydrogen atom or a methyl radical, symbols $R^5$ and $R^8$ stand each for a methyl radical, symbols $R^6$ and $R^7$ can be identical or different and designate each a hydrogen atom or a methyl radical and, either symbol $R^4$ represents a methyl radical and symbol $R^3$ stands for a hydrogen atom or a methyl radical, or symbols $R^3$ and $R^4$ represent each a methylene radical belonging to a ring such as indicated by the dotted line, with the proviso that the following combinations are excluded:
1. $R^1=R^2=R^3=R^6=R^7=H$, or
2. $R^1=R^2=R^3=H$ and $R^6$ or $R^7=CH_3$, or
3. $R^2=CH_3$ and $R^3=R^6=R^7=H$, or
4. $R^2=CH_3$ and $R^3=H$ and $R^6$ or $R^7=CH_3$, or
5. $R^1=R^3=CH_3$, or
6. $R^3=R^4=CH_2$ and $R^6$ or $R^7=CH_3$;

or wherein
b) indexes m and n are different and define each an integer number equal to 0 or 1, symbol $R^2$ stands for a hydrogen atom or a methyl radical, symbols $R^1$ and $R^3$ designate each a hydrogen atom, symbol $R^4$ represents a methyl radical and, either symbols $R^5$ and $R^6$ are identical (n=1) and represent each a methylene radical belonging to a ring such as indicated by the dotted line, $R^7$ representing a hydrogen atom and $R^8$ a methyl radical, or symbol $R^5$ stands for a methyl radical and symbol $R^6$ for a hydrogen atom, $R^7$ and $R^8$ being then identical (m=1) and designating each a methylene radical belonging to a ring such as indicated by the dotted line;

or any mixture of two or more structural isomers of formula (I).

2. The method of claim 1 which further comprises, as a compound of formula (I), a compound of formula

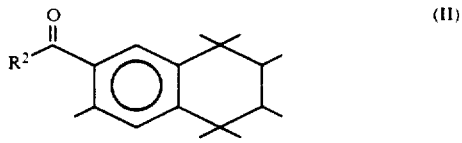

(II)

wherein symbol $R^2$ stands for a hydrogen atom or a methyl radical.

3. The method of claim 1 which further comprises selecting, as a compound of formula (I), one of the following compounds:
a) 5,6,7,8-tetrahydro-1,3,5,5,8,8-hexamethyl-2-naphthalenecarbaldehyde
b) 5,6,7,8-tetrahydro-3,4,5,5,8,8-hexamethyl-2-naphthalenecarbaldehyde
c) 5,6,7,8-tetrahydro-1,3,5,5,6,8,8-heptamethyl-2-naphthalenecarbaldehyde
d) 5,6,7,8-tetrahydro-3,4,5,5,7,8,8-heptamethyl-2-naphthalenecarbaldehyde
e) 5,6,7,8-tetrahydro-1,3,5,5,7,8,8-heptamethyl-2-naphthalenecarbaldehyde
f) 5,6,7,8-tetrahydro-3,4,5,5,6,8,8-heptamethyl-2-naphthalenecarbaldehyde
g) 1,2,6,7,8,8a-hexahydro-3,6,6,8a-tetramethyl-4-acenaphthylenecarbaldehyde
h) (1,2,6,7,8,8a-hexahydro-3,6,6,8a-tetramethyl-4-acenaphthylenyl)ethanone or any mixture of compounds a) and b), or c) and d), or e) and f).

4. The method of claim 1 which further comprises selecting, as a compound of formula (I), a mixture of following compounds i) and j) or k) and l):
i) 2,3,3a,4,5,9b-hexahydro-5,5,8,9b-tetramethyl-1H-benz[e]indene-7-carbaldehyde
j) 2,3,3a,4,5,9b-hexahydro-5,5,7,9b-tetramethyl-1H-benz[e]indene-8-carbaldehyde
k) 1-(2,3.3a,4,5,9b-hexahydro-5,5,8,9b-tetramethyl-1H-benz[e]inden-7-yl)-1-ethanone
l) 1-(2,3,3a,4,5,9b-hexahydro-5,5,7,9b-tetramethyl-1H-benz[e]inden-8-yl)-1-ethanone.

5. The method of claim 2 which further comprises selecting, as a compound of formula (I), one of the following compounds:
m) trans-5,6,7,8-tetrahydro-3,5,5,6,7,8,8-heptamethyl-2-naphthalenecarbaldehyde
n) cis-5,6,7,8-tetrahydro-3,5,5,6,7,8,8-heptamethyl-2-naphthalenecarbaldehyde
o) trans-(5,6,7,8-tetrahydro-3,5,5,6,7,8,8-heptamethyl-2-naphthyl)-1-ethanone or any mixture of compounds m) and n) or of compound o) with cis-(5,6,7,8-tetrahydro-3,5,5,6,7,8,8-heptamethyl-2-naphthyl)-1-ethanone.

6. A perfuming composition containing as an active ingredient a compound of formula (I) according to claim 1.

7. A perfumed article containing as an active ingredient a compound of formula (I) according to claim 1.

8. As a perfumed article according to claim 7, a perfume or Cologne, an after-shave lotion, a soap, a bath or shower gel, a body deodorant, a cosmetic preparation, a detergent or fabric softener.

* * * * *

UNITED STATES PATENT AND TRADEMARK OFFICE
CERTIFICATE OF CORRECTION

PATENT NO. : 5,185,318　　　　　　　　　　　Page 1 of 2
DATED : February 9, 1993
INVENTOR(S) : Charles Fehr and Jose Galindo It is certified that error appears in the above-indentified patent and that said Letters Patent is hereby corrected as shown below:

Columns 15, 16, and 17, the formulas should read:

Column 15:

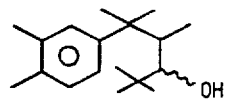

Column 16:

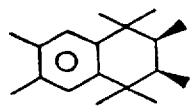

(III b2.)

UNITED STATES PATENT AND TRADEMARK OFFICE
CERTIFICATE OF CORRECTION

PATENT NO. : 5,185,318  
DATED : February 9, 1993  
INVENTOR(S) : Charles Fehr and Jose Galindo Page 2 of 2

It is certified that error appears in the above-indentified patent and that said Letters Patent is hereby corrected as shown below:

Column 17:

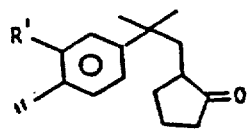 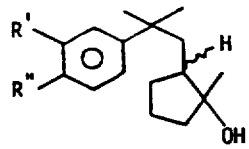

(mixture)

Column 33, Example 12, in the table, should read: "...1% $\gamma$-Undecalactone..."

Column 35, Claim 2, should read: "...comprises, selecting as ..."

Signed and Sealed this

Sixteenth Day of May, 1995

Attest:

BRUCE LEHMAN

Attesting Officer   Commissioner of Patents and Trademarks